United States Patent [19]

Nohira et al.

[11] Patent Number: 5,328,639
[45] Date of Patent: Jul. 12, 1994

[54] FLUOROALKANE DERIVATIVE, ITS COMPOSITION AND LIQUID CRYSTAL DEVICE USING THE SAME

[75] Inventors: Hiroyuki Nohira, Urawa; Masanao Kamei, Annaka; Shinichi Nakamura, Urawa; Kazuharu Katagiri, Tama; Masahiro Terada, Atsugi; Masataka Yamashita, Hiratsuka; Yoko Yamada, Atsugi; Kenji Shinjo, Atsugi; Takashi Iwaki, Atsugi; Chieko Hioki, Kawasaki; Akio Yoshida, Chigasaki; Toshiharu Uchimi, Atsugi, all of Japan

[73] Assignee: Canon Kabushiki Kaisha, Tokyo, Japan

[21] Appl. No.: 999,556

[22] Filed: Dec. 31, 1992

Related U.S. Application Data

[63] Continuation of Ser. No. 403,046, Sep. 1, 1989, abandoned, which is a continuation of Ser. No. 118,889, Nov. 10, 1987, abandoned.

[30] Foreign Application Priority Data

Nov. 10, 1986 [JP] Japan ............................. 61-267044
Jan. 12, 1987 [JP] Japan ............................. 62-5827
Jan. 12, 1987 [JP] Japan ............................. 62-5829
Oct. 26, 1987 [JP] Japan ............................. 62-271118

[51] Int. Cl.$^5$ .................. C09K 19/34; C09K 19/20; C07D 239/02; C07C 69/76
[52] U.S. Cl. .................. 252/299.61; 252/299.63; 252/299.65; 252/299.67; 544/298; 544/318; 544/335; 560/65
[58] Field of Search .................. 560/65, 106; 252/299.67, 299.01, 299.61, 299.63, 299.65; 544/298, 318, 335

[56] References Cited

U.S. PATENT DOCUMENTS

| | | | |
|---|---|---|---|
| 4,576,732 | 3/1986 | Isogai et al. | 252/299.01 |
| 4,592,858 | 6/1986 | Higuchi et al. | 252/299.66 |
| 4,613,209 | 9/1986 | Goodby et al. | 252/299.65 |
| 4,615,586 | 10/1986 | Geary et al. | 350/350 |
| 4,695,650 | 9/1987 | Walba et al. | 252/299.67 |
| 4,695,651 | 9/1987 | Higuchi et al. | 252/299.66 |
| 4,723,005 | 2/1988 | Huynh-Ba et al. | 252/299.67 |
| 4,725,688 | 2/1988 | Taguchi et al. | 252/299.61 |
| 4,728,458 | 3/1988 | Higuchi et al. | 252/299.01 |
| 4,732,699 | 3/1988 | Higuchi et al. | 252/299.66 |
| 4,798,680 | 1/1989 | Nohira et al. | 252/299.01 |
| 4,834,904 | 5/1989 | Krause et al. | 252/299.61 |
| 5,139,697 | 8/1992 | Togano et al. | 252/299.67 |
| 5,238,601 | 8/1993 | Shinjo et al. | 252/299.63 |
| 5,240,637 | 8/1993 | Shinjo et al. | 252/299.61 |

FOREIGN PATENT DOCUMENTS

| | | |
|---|---|---|
| 0191600 | 2/1986 | European Pat. Off. . |
| 0237007 | 3/1987 | European Pat. Off. . |
| 225195 | 6/1987 | European Pat. Off. ........ 252/299.61 |
| 239444 | 9/1987 | European Pat. Off. ........ 252/299.65 |
| 248335 | 12/1987 | European Pat. Off. ........ 252/299.61 |
| 0293910 | 6/1988 | European Pat. Off. . |
| 0301602 | 8/1988 | European Pat. Off. . |
| 3525015 | 1/1986 | Fed. Rep. of Germany ...................... 252/299.66 |
| 3604905 | 9/1986 | Fed. Rep. of Germany . |
| 240385 | 10/1986 | Fed. Rep. of Germany ...................... 252/299.61 |
| 3515373 | 11/1986 | Fed. Rep. of Germany ...................... 252/299.61 |
| 3518734 | 11/1986 | Fed. Rep. of Germany ...................... 252/299.61 |

OTHER PUBLICATIONS

J. Am. Chem. Soc., vol. 108, No. 17 (Aug. 20, 1986) 5210:21.

Primary Examiner—Philip Tucker
Attorney, Agent, or Firm—Fitzpatrick, Cella, Harper & Scinto

[57] ABSTRACT

A liquid crystal composition, comprising: at least one optically active mesomorphic compound having an asymmetric carbon atom to which a fluorine atom is directly bonded.

9 Claims, 4 Drawing Sheets

FLUOROALKANE DERIVATIVE, ITS COMPOSITION AND LIQUID CRYSTAL DEVICE USING THE SAME

This application is a continuation of U.S. application Ser. No. 403,046, filed Sep. 1, 1989, now abandoned, which is a continuation of U.S. application Ser. No. 118,889, filed Nov. 10, 1987, now abandoned.

FIELD OF THE INVENTION AND RELATED ART

The present invention relates to a novel mesomorphic compound and, more particularly, to a fluoroalkane derivative as an optically active mesomorphic compound, a chiral smectic liquid crystal composition containing the same and a liquid crystal device using the liquid crystal composition.

The present invention further relates to a liquid crystal composition used in a liquid crystal device, such as a liquid crystal display device, a liquid crystal-optical shutter, etc., and particularly to such a liquid crystal composition having an improved alignment state and improved driving characteristics inclusive of an improved responsive characteristic to an applied electric field.

It has been proposed to use a liquid crystal device showing bistability by Clark and Lagerwall (Japanese Laid-Open Patent Appln. No. 107216/1981; U.S. Pat. No. 4,367,924, etc.). As the bistable liquid crystal, a ferroelectric liquid crystal showing a chiral smectic C phase (SmC*) or H phase (SmH*) is generally used. The ferroelectric liquid crystal shows bistable states including a first optically stable state and a second optically stable state in response to an electric field applied thereto, so that it is oriented to the first optically stable state in response to one electric field vector and to the second optically stable state in response to the other electric field vector, unlike a conventional TN-type liquid crystal, and the resultant states are retained in the absence of an electric field. In addition to the bistability as described above, the ferroelectric liquid crystal has an important advantage that it has a high response speed.

Further, since a material used as a ferro-electric liquid crystal has an asymmetry, it can be used as a functional material to be used in the following types of optical devices in addition to the use as a ferroelectric liquid crystal material:

1) Those utilizing a cholesteric-nematic phase transition in a liquid crystal state (J. J. Wysoki, A. Adams and W. Haas: Phys. Rev. Lett., 20, 10204 (1968));

2) Those utilizing a guest-host effect of the White-Taylor type in a liquid crystal state (D. L. White and G. N. Taylor: J. Appl. Phys. 45, 4718 (1974)).

These optical devices are important as display devices and modulation devices, while the explanation of the individual systems is left to the respective references and omitted.

It has been understood that, in a method utilizing an electric field-responsive optical effect of a liquid crystal, it is desirable to introduce a polar group or a group providing a polar bond in a compound constituting the liquid crystal in order to enhance the responsive characteristic of the liquid crystal. Particularly, with respect to a ferroelectric liquid crystal, it has been known that the responsive speed is proportional to its spontaneous polarization, so that it is desired to increase the spontaneous polarization in order to realize a high response speed. From this viewpoint, P. Keller et al have shown that it is possible to provide a higher response speed by introducing a chlorine atom directly connected to an asymmetric carbon atom. However, such a chlorine atom directly introduced to an asymmetric carbon atom involves problems that it is chemically unstable and lowers the stability of a liquid crystal phase as it has a large atomic radius.

On the other hand, many of optically active functional compounds for use in optical devices as described above are synthesized through an intermediate which per se is optically active. Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives. However, it has been seldome to incorporate a polar group into such an intermediate. Partly for this reason, the above mentioned method of introducing a polar group directly to an asymmetric carbon atom has not been utilized very effectively.

Further, ferroelectric liquid crystal materials developed heretofore have not fully satisfied required characteristics for a liquid crystal device, inclusive of low-temperature operation characteristic and high-speed responsive characteristic.

Furthermore, in a known ferroelectric liquid crystal device showing bistability, an ideal uniform alignment state of liquid crystal molecules has not been satisfactorily realized, so that it is a present state that sufficient performances have not been attained. In order to provide a uniform alignment state, it has been proposed to align ferroelectric liquid crystal molecules showing bistability in the presence of a surface subjected to rubbing or oblique vapor deposition. We have already obtained a knowledge that a uniform alignment state of a bistable ferro-electric liquid crystal can be formed by using a substrate which has been subjected to the above mentioned rubbing or oblique vapor deposition. According to our experiments, however, the thus obtained bistable state is not necessarily an ideal bistable state as published by Clark and Lagerwall in the above mentioned references.

More specifically, according to Clark and Lagerwall, a chiral smectic phase with a non-helical structure realizing bistability provide a tilt angle (angle $\theta$ in FIG. 3 described hereinafter) which is expected to be equal to a tilt angle in a chiral smectic phase with a helical structure (angle Ⓗ which is one half the apical angle of a cone shown in FIG. 2 described hereinafter). In fact, however, the tilt angle $\theta$ in the non-helical structure is smaller than the tilt angle Ⓗ in the helical structure. Furthermore, it has been found that the smaller tilt angle $\theta$ in the non-helical structure than the tilt angle Ⓗ in the helical structure is attributable to the presence of a twist alignment of liquid crystal molecules in the non-helical structure. More specifically, in a chiral smectic phase with a non-helical structure, liquid crystal molecules are arranged in such a manner that their molecular axes are continuously twisted from the axis 82 of a molecular adjacent to one substrate to the axis 83 of a molecular adjacent to the other substrate with a twist angle $\delta$ as shown in FIG. 8, and the twist arrangement causes a smaller tilt angle $\theta$ in the non-helical structure than the tilt angle Ⓗ in the helical structure.

In FIG. 8, a line 81 represents a uniaxial orientation axis provided to the pair of substrates as by rubbing or oblique vapor deposition treatment.

Incidentally, the transmittance of a liquid crystal device utilizing birefringence of a liquid crystal is expressed by the following equation under the conditions of right angle cross nicols:

$$I/I_0 = \sin^2 4\theta \cdot \sin^2(\Delta n \cdot d \cdot \pi / \lambda),$$

wherein $I_0$ denotes the intensity of incident light; I, the intensity of transmitted light, $\theta$, a tilt angle; $\Delta n$, a refractive index anisotropy; d, the thickness of a liquid crystal layer; and $\lambda$, the wavelength of the incident light. The tilt angle $\theta$ used herein is obtained as one half of the angle between the average molecular axes of the liquid crystal molecules in the first and second orientation states in twisted alignment state described above. The above equation shows that a maximum transmittance is attained when the tilt angle $\theta$ is 22.5°, whereas the tilt angle $\theta$ in the non-helical structure providing bistability is on the order of 10° at the most. As a result, the transmittance obtained when applied to a display apparatus is on the order of 3–5%, thus being insufficient

SUMMARY OF THE INVENTION

A principal object of the present invention is, in view of the above problems, to provide a mesomorphic compound having an enhanced electric field-responsive characteristic in an liquid crystal state by introducing a fluorine atom, which is stable and has a large dipole moment, directly to an asymmetric carbon atom.

Another object of the present invention is to provide a liquid crystal composition comprising at least one species of the mesomorphic compound.

A further object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 266, 146 (1964), and a liquid crystal composition containing at least one species of the mesomorphic compound.

Another object of the present invention is to provide a liquid crystal composition showing display characteristics, which cannot be obtained by a single mesomorphic compound, such as low temperature characteristic, and high-speed responsiveness, by mixing a specific mesomorphic compound, and a liquid crystal device using the liquid crystal composition.

A further object of the present invention is to provide a liquid crystal composition showing an increased tilt angle in a chiral smectic phase in a non-helical structure, and a liquid crystal device using the liquid crystal composition.

According to the present invention, there is provided a

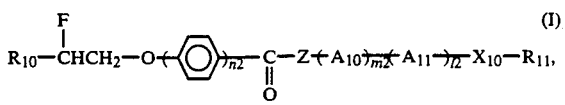

wherein $R_{10}$ denotes an alkyl group having 1–16 carbon atoms; C* denotes an asymmetric carbon atom; $R_{11}$ denotes an alkyl group having 1–16 carbon atoms; Z denotes —O— or —S—; $X_{10}$ denotes a single bond, —O—, or

$A_{10}$ and $A_{11}$ denote a phenylene group

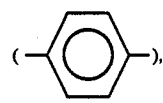

a cyclohexylene group

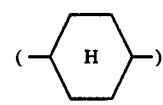

or a pyrimidinylene group

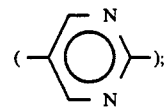

n2 is 1 or 2; l2 and m2 are 0 or a positive integer satisfying the relation l2+m2=1 or 2.

The present invention further provides a liquid crystal composition containing at least one species of the above-mentioned optically active fluoroalkane derivative; and also a liquid crystal device comprising a pair of electrode plates and the liquid crystal composition disposed between the electrode plates.

According to another aspect of the present invention there is provided a liquid crystal composition comprising:

at least one optically active mesomorphic compound having an asymmetric carbon atom to which a fluorine atom is directly bonded (herein after referred to as "F-type mesomorphic compound"), preferably one represented by the following formula (3):

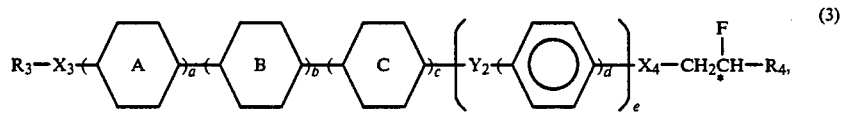

wherein $Y_2$ denotes

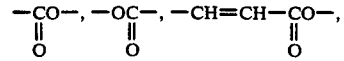

or

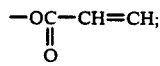

$X_3$ denotes a single bond,

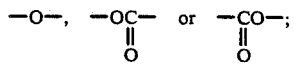

$X_4$ denotes

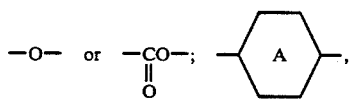

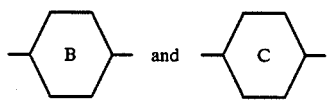

are respectively

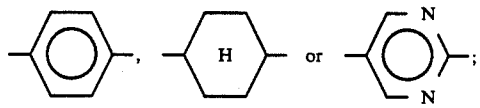

$R_3$ and $R_4$ respectively denote a linear or branched alkyl, alkoxyalkyl or halogenated alkyl group having 1–16 carbon atoms capable of including an asymmetric carbon atom; a, b, c and d are respectively 0, 1 or 2; e is 0 or 1; and C* denotes an asymmetric carbon atom; and at least one optically active mesomorphic compound having an optically active group represented by the following formula (1):

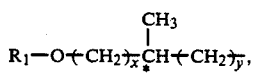  (1)

wherein $R_1$ denotes a lienar or branched alkyl group having 1–18 carbon atoms, x is 0 or 1, y is an integer of 0–8, and C* denotes an asymmetric carbon atom; preferably at least one optically active mesomorphic compound represented by the following formula (2):

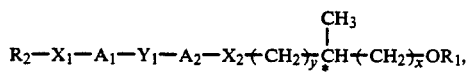  (2)

wherein $X_1$ and $X_2$ respectively denote a single bond,

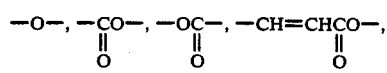

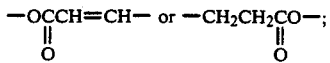

$Y_1$ denotes a single bond

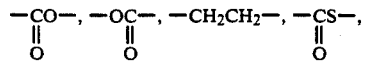

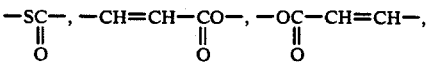

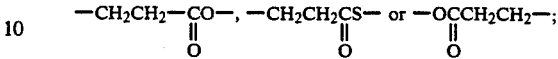

$A_1$ and $A_2$ denote a divalent 6-membered ring group capable of having a substituent (examples of the substituent may include alkyl group, alkoxy group, halogen atom of chlorine, bromine or fluorine, or cyano group, and the divalent group containing a 6-membered ring may be example be

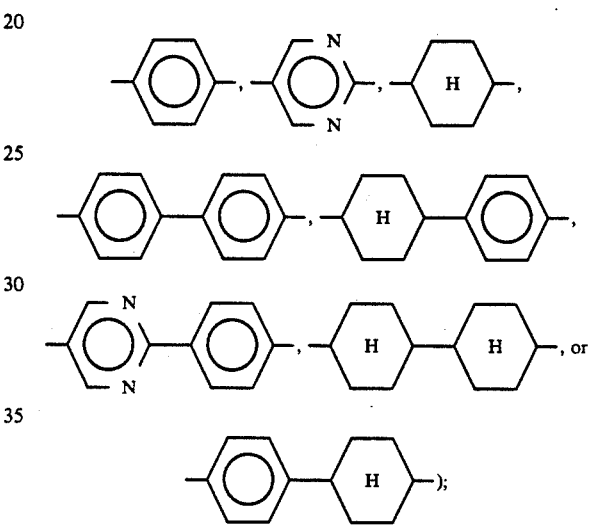

$R_2$ and $R_1$ denote a linear or branched alkyl group having 4–16 carbon atoms and 1–18 carbon atoms, respectively; y is an integer of 0–8, x is 0 or 1, and C* denotes an asymmetric carbon atom. The present invention further provides a liquid crystal device comprising a pair of electrode plates and the above liquid crystal composition disposed between the electrode plates.

According to still another aspect of the present invention, there is provided a liquid crystal composition, comprising: at least one mesomorphic compound (A) in the form of an ester having an optically active asymmetric carbon atom to which a fluorine atom is directly bonded in its carboxylic acid moiety, and at least one mesomorphic compound (B) in the form of an ester having an optically active asymmetric carbon atom to which a fluorine atom is directly bonded in its alcohol moiety.

The mesomorphic compound (A) may preferably be one represented by the following formula (4), and the mesomorphic compound (B) may preferably be one represented by the formula (5):

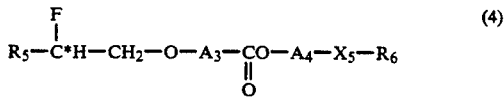  (4)

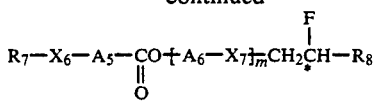

In the formulas (4) and (5), $R_5$, $R_6$, $R_7$ and $R_8$ denote a linear or branched alkyl group having 1-16 carbon atoms; C* denotes an asymmetric carbon atom; $X_5$ and $X_6$ denote a single bond, —O— or —COO—; $X_7$ denotes —O— or —COO—; m is 0 or 1; $A_3$, $A_4$, $A_5$ and $A_6$ denote a group containing a 6-membered ring capable of having a substituent. $A_3$ and $A_4$ may preferably be one represented by

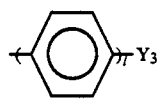

(wherein $Y_3$ denotes a single bond, —CH=CH— or —CH$_2$CH$_2$—; l is 1 or 2), and $A_5$ and $A_6$ may preferably be one represented by

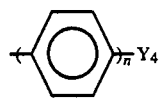

(wherein $Y_4$ denotes a single bond, —CH=CH— or —CH$_2$CH$_2$—, n is 1 or 2).

With reference to the above formulas (4) and (5), the carboxylic acid moiety herein refers to the portion (A) of the ester shown below:

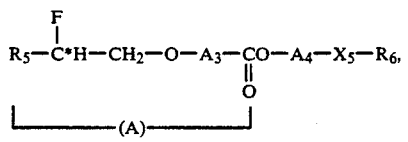

and the alcohol moiety refers to the portion (B) of the ester shown below:

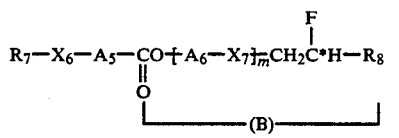

Thus, the present invention is based on the finding that the liquid crystal composition comprising at least mesomorphic compound (A) and at least one mesomorphic compound (B) each in the form of an ester but having their asymmetric carbon atoms directly connected to a fluorine atom in their carboxylic acid moiety and alcohol moiety, respectively, provides display characteristic which cannot be obtained by a single mesomorphic compound through improvement in low-temperature operation characteristic and high-speed responsive characteristic.

According to another aspect of the present invention, there is provided a liquid crystal composition comprising at least one mesomorphic compound (C) showing a chiral smectic phase with a spontaneous polarization $P_S$ (at a temperature 15° C. below the upper limit temperature of the chiral smectic phase) of 8 nC/cm² or above, preferably 20 nC/cm² or above, and at least one mesomorphic compound (D) showing a chiral smectic phase with a spontaneous polarization $P_S$ of −8 nC/cm² or below, preferably −20 nC/cm² or below.

The above chiral smectic phase may represent chiral smectic C phase (SmC*), H phase (SmH*), I phase (SmI*) or G phase (SmG*). The above-mentioned spontaneous polarization is one measured at a temperature (T° C.) which is 15° C. below the upper limit temperature of the chiral smectic phase ($T_C$ ° C.) with respect to a mesomorphic compound concerned (Thus, $T_C - T = 15$ (°C.)). More specifically, with respect to a mesomorphic compound showing SmC*, the spontaneous polarization $P_S$ of the mesomorphic compound is measured at a temperature 15° C. below the upper limit temperature of the SmC*.

The above-mentioned twist angle and twist direction due to twist alignment are determined by the surface condition of the substrates or electrode plates contacting the liquid crystal and interaction between liquid crystal molecules. According to a ferroelectric liquid crystal device using the above-mentioned liquid crystal composition, the twist alignment can be removed. In such a ferroelectric liquid crystal device having removed the twist alignment, a maximum transmittance/interruption contrast is attained under right-angle cross nicols while a maximum contrast is attained under non-right-angle cross nicols with bistable states in a twist alignment. In such a liquid crystal device with a twist alignment, there is observed a view-angle dependency that the contrast varies depending on the direction of observation. Along with the removal of the twist alignment, it is also possible to remove such a view angle dependency.

These and other objects, features and advantages of the present invention will become more apparent upon a consideration of the following description of the preferred embodiments of the present invention taken in conjunction with the accompanying drawings. In the description appearing hereinafter, "part(s)" and "%" used for describing compositions or quantitative ratios are by weight unless otherwise noted specifically.

DETAILED DESCRIPTION OF PREFERRED EMBODIMENTS

Figure 1:
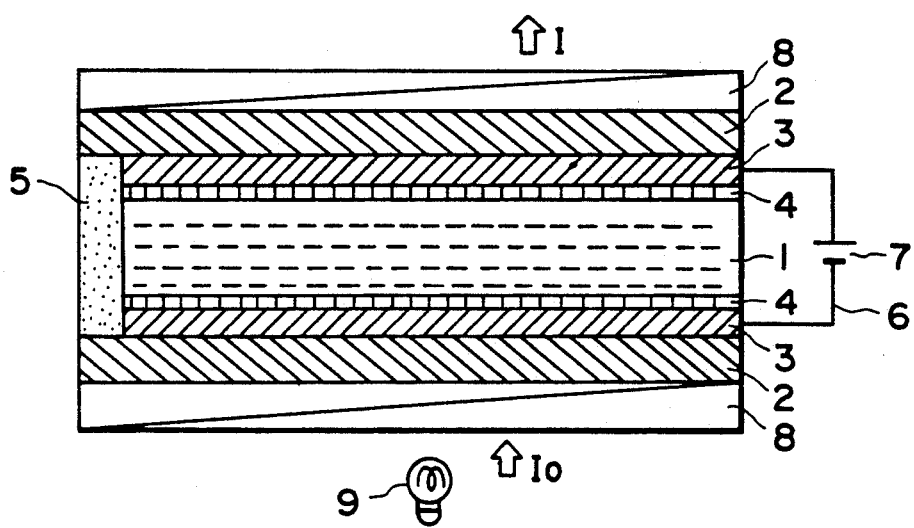
FIG. 1 is a sectional view of an embodiment of the ferroelectric liquid crystal device according to the present invention.

We have discovered that a liquid crystal device with an enlarged temperature range for providing smectic C* phase, an increased response speed and improved display characteristics can be obtained by using a mixture of F (fluorine)-type mesomorphic compound and a mesomorphic compound represented by the above formula (1) than a liquid crystal device using a single material of these mesomorphic compounds.

Mesomorphic compounds used in the present invention may include F-type mesomorphic compounds in general (preferably those represented by the formula (3)) and mesomorphic compounds having an optically active group represented by the formula (1) (preferably those represented by the formula (2)).

Specific examples of the mesomorphic compounds represented by the formulas (2) and (3) are shown in the tables 1 and 2 below with their structural formulas and phase transition temperatures. It should be noted however that the mesomorphic compounds usable in the present invention are not limited to those specifically shown in the tables.

In the Tables and the description appearing hereinafter, the symbols used for describing phase-transition respectively denote the following phases.

Cryst.: crystal phase,
SmA: smectic A phase,
SmB: smectic B phase,
SmC*: chiral smectic C phase,
N: nematic phase,
Ch.: cholesteric phase,
Iso.: isotropic phase, and
Sm1, Sm2, Sm3: smectic phase (un-identified) other than SmA and SmC*.

TABLE 1

$$R_2-X_1-A_1-Y_1-A_2-X_2(CH_2)_y\overset{*}{C}H(CH_3)(CH_2)_xOR_1$$

| Compound | $R_2$ | $R_1$ | $X_1$ | $A_1$ | $Y_1$ | $A_2$ | $X_2$ | y | x | Phase transition temperature (°C.) |
|---|---|---|---|---|---|---|---|---|---|---|
| 1 | $C_{10}H_{21}-$ | $C_2H_5-$ | $-O-$ | phenyl | $-CO-O-$ | phenyl | $-O-$ | 1 | 0 | Cryst. ⇌(36.7/−4) SmA ⇌(39.4/39.0) Iso.; SmA ⇌(27.8/9) SmC*; SmC* →S3 |
| 2 | $C_8H_{17}-$ | $C_5H_{11}-$ | — | cyclohexyl | $-O-CO-$ | biphenyl | $-O-$ | 1 | 0 | Cryst. ⇌(25.8/25.2) Sm2 ⇌(130.8/130.5) SmA ⇌(197.7/197.3) Iso. |
| 3 | $C_8H_{17}-$ | $C_5H_{11}-$ | — | cyclohexyl | $-CO-O-$ | phenyl | $-O-$ | 3 | 0 | Cryst. ⇌(44.9/23.7) Sm2 ⇌(93.1/91.8) SmA ⇌(111.1/109.6) Iso. |
| 4 | $C_{16}H_{33}-$ | $C_{12}H_{25}-$ | $-O-$ | biphenyl | $-CO-O-$ | phenyl | $-O-$ | 1 | 0 | Cryst. ⇌(100.4/80.5) SmC* ⇌(117.4/115.6) SmA ⇌(120.8/117.9) Iso. |
| 5 | $C_{10}H_{21}-$ | $C_8H_{17}-$ | $-OC=O-$ | biphenyl | $-CO-O-$ | phenyl | $-O-$ | 1 | 0 | Cryst. ⇌(42.2/26.7) SmC* ⇌(93.1/89.8) Iso.; SmC* →(47.1) Sm2 |
| 6 | $C_{10}H_{21}-$ | $C_2H_5-$ | $-OC=O-$ | biphenyl | $-O-CO-$ | phenyl | $-O-$ | 1 | 0 | Cryst. ⇌(15.8/12.5) SmC* ⇌(86.0/83.2) SmA ⇌(107.7/104.8) Iso.; SmC* →(57.5) Sm3 |
| 7 | $C_{10}H_{21}-$ | $C_5H_{11}-$ | $-O-$ | phenyl | $-CO-O-$ | biphenyl | $-CO-O-$ | 1 | 0 | Cryst. ⇌(55.1/14) SmC* ⇌(93.5/91.2) SmA ⇌(143.0/142.5) Iso.; SmC* →(30.1) Sm3 |
| 8 | $C_8H_{17}-$ | $C_5H_{11}-$ | — | cyclohexyl | $-CO-O-$ | phenyl | $-CO-O-$ | 2 | 0 | Cryst. ⇌(28.3/−10) Sm3 ⇌(47.1/46.4) SmA ⇌(66.0/65.0) Iso. |

TABLE 1-continued $$R_2-X_1-A_1-Y_1-A_2-X_2-(CH_2)_y-\underset{\underset{CH_3}{|}}{CH}-(CH_2)_x-OR_1 \quad (2)$$

| Compound | $R_2$ | $R_1$ | $X_1$ | $A_1$ | $Y_1$ | $A_2$ | $X_2$ | y | x | Phase transition temperature (°C) |
|---|---|---|---|---|---|---|---|---|---|---|
| 9 | $C_{10}H_{21}-$ | $C_2H_5-$ | $-O-$ | phenyl | $-CH_2CH_2-$ | phenyl | $-O-$ | 1 | 0 | Cryst. $\underset{33.6}{\overset{44.7}{\rightleftarrows}}$ Iso. |
| 10 | $C_{10}H_{21}-$ | $C_5H_{11}-$ | $-OC(=O)-$ | biphenyl | $-OC(=O)-$ | phenyl | $-O-$ | 1 | 0 | Cryst. $\underset{14.6}{\overset{37.8}{\rightleftarrows}}$ SmC* $\underset{91.1}{\overset{94.4}{\rightleftarrows}}$ Ch $\underset{92.2}{\overset{95.2}{\rightleftarrows}}$ Iso. |
| 11 | $C_{10}H_{21}-$ | $C_2H_5-$ | $-O-$ | phenyl | $-(CH_2)_2CO(=O)-$ | phenyl | $-O-$ | 1 | 0 | Cryst. $\underset{41.0}{\overset{54.1}{\rightleftarrows}}$ Iso. |
| 12 | $C_6H_{13}-$ | $C_8H_{17}-$ | $-O-$ | phenyl | $-OC(=O)-$ | phenyl | $-OC(=O)-$ | 0 | 0 | Cryst. $\overset{39}{\rightarrow}$ Iso. |
| 13 | $C_8H_{17}-$ | $C_{12}H_{25}-$ | — | pyrimidine | — | — | $-O-$ | 2 | 0 | Cryst. $\underset{-10.1}{\overset{37.0}{\rightleftarrows}}$ Iso., $\overset{-1.4}{\rightarrow}$ SmI |
| 14 | $C_{10}H_{21}-$ | $C_2H_5-$ | $-O-$ | phenyl | $-CH=CH-CO(=O)-$ | phenyl | $-O-$ | 1 | 0 | Cryst. $\underset{27}{\overset{55.7}{\rightleftarrows}}$ SmC* $\underset{35.3}{\overset{71.7}{\rightleftarrows}}$ SmA $\underset{81.4}{\overset{82.6}{\rightleftarrows}}$ Iso., Sm3 |
| 15 | $C_{12}H_{25}-$ | $C_8H_{17}-$ | $-O-$ | phenyl | $-CS(=O)-$ | phenyl | $-O-$ | 1 | 0 | Cryst. $\underset{20.7}{\overset{35.1}{\rightleftarrows}}$ SmC* $\underset{43.4}{\overset{46.2}{\rightleftarrows}}$ Iso. |
| 16 | $C_{12}H_{25}-$ | $C_5H_{11}-$ | $-O-$ | phenyl | $-CO(=O)-$ | phenyl | $-O-$ | 1 | 0 | Cryst. $\underset{3.3}{\overset{41.8}{\rightleftarrows}}$ SmA $\underset{43.4}{\overset{46.6}{\rightleftarrows}}$ Iso. |
| 17 | $C_8H_{17}-$ | $C_2H_5-$ | $-O-$ | phenyl | $-CO(=O)-$ | phenyl | $-CH=CHCO(=O)-$ | 1 | 0 | Cryst. $\underset{7.4}{\overset{69.0}{\rightleftarrows}}$ SmA $\underset{79.9}{\overset{81.3}{\rightleftarrows}}$ Iso. |
| 18 | $C_{10}H_{21}-$ | $C_5H_{11}-$ | $-O-$ | biphenyl | $-CO(=O)-$ | phenyl | $-CO(=O)-$ | 2 | 0 | Cryst. $\underset{31}{\overset{63}{\rightleftarrows}}$ Sm3 $\underset{55}{\overset{64}{\rightleftarrows}}$ SmC* $\underset{130}{\overset{132}{\rightleftarrows}}$ SmA $\underset{148}{\overset{152}{\rightleftarrows}}$ Iso. |

TABLE 1-continued $$R_2-X_1-A_1-Y_1-A_2-X_2(CH_2)_y\overset{CH_3}{\underset{*}{C}H}(CH_2)_xOR_1$$

| Compound | $R_2$ | $R_1$ | $X_1$ | $A_1$ | $Y_1$ | $A_2$ | $X_2$ | y | x | Phase transition temperature (°C.) |
|---|---|---|---|---|---|---|---|---|---|---|
| 19 | $C_{12}H_{25}$— | $C_5H_{11}$— | —O— | phenyl | $-\underset{\parallel}{C}-O-$<br>O | phenyl | $-\underset{\parallel}{C}-O-$<br>O | 5 | 0 | Cryst. $\underset{11.7}{\overset{31.2}{\rightleftarrows}}$ SmC* $\underset{38.5}{\overset{38.6}{\rightleftarrows}}$ SmA $\underset{}{\overset{40.2}{\rightleftarrows}}$ Iso. |
| 20 | $C_{12}H_{25}$— | $C_5H_{11}$— | —O— | phenyl | $-\underset{\parallel}{C}-O-$<br>O | phenyl | —O— | 5 | 0 | Cryst. $\underset{}{\overset{29.7}{\rightleftarrows}}$ Sm2 $\underset{34.2}{\overset{36.4}{\rightleftarrows}}$ SmC* $\underset{55.1}{\overset{56.6}{\rightleftarrows}}$ Iso. |
| 21 | $C_{10}H_{21}$— | $C_5H_{11}$— | $-O-\underset{\parallel}{C}-$<br>O | cyclohexyl | $-O-\underset{\parallel}{C}-$<br>O | phenyl | —O— | 1 | 0 | Cryst. $\underset{35.3}{\overset{42.8}{\rightleftarrows}}$ Sm1 $\underset{}{\overset{46.0}{\rightleftarrows}}$ Iso. |
| 22 | $C_8H_{17}$— | $C_5H_{11}$— | —O— | phenyl | $-S-\underset{\parallel}{C}-$<br>O | biphenyl | —O— | 1 | 0 | Cryst. $\underset{38.1}{\overset{72.6}{\rightleftarrows}}$ Sm2 $\underset{81.9}{\overset{82.7}{\rightleftarrows}}$ SmC* $\underset{142.9}{\overset{143.4}{\rightleftarrows}}$ Ch $\underset{151.3}{\overset{151.8}{\rightleftarrows}}$ Iso. |
| 23 | $C_{10}H_{21}$— | $C_2H_5$— | —O— | biphenyl | $-\underset{\parallel}{C}-O-$<br>O | phenyl | $-\underset{\parallel}{C}-O-$<br>O | 1 | 0 | Cryst. $\underset{32}{\overset{77}{\rightleftarrows}}$ Sm3 $\underset{}{\overset{41}{\rightleftarrows}}$ SmC* $\underset{134}{\overset{137}{\rightleftarrows}}$ SmA $\underset{174}{\overset{177}{\rightleftarrows}}$ Iso. |
| 24 | $C_5H_{11}$— | $C_{12}H_{25}$— | —O— | biphenyl | $-\underset{\parallel}{C}-O-$<br>O | phenyl | —O— | 1 | 0 | Cryst. $\underset{61.5}{\overset{89.2}{\rightleftarrows}}$ Sm3 $\underset{65.5}{\overset{70.9}{\rightleftarrows}}$ SmC* $\underset{152.7}{\overset{155.6}{\rightleftarrows}}$ SmA $\underset{}{\rightleftarrows}$ Iso. |
| 25 | $C_{10}H_{21}$— | $C_2H_5$— | —O— | phenyl | $-(CH_2)_2\underset{\parallel}{C}-$<br>O | phenyl | —O— | 1 | 0 | Cryst. $\underset{18.3}{\overset{32.5}{\rightleftarrows}}$ Iso. |

TABLE 1-continued $$R_2-X_1-A_1-Y_1-A_2-X_2+CH_2\overset{*}{\underset{y}{)}}\overset{CH_3}{\underset{|}{CH}}+CH_2\overset{}{\underset{x}{)}}OR_1$$

| Compound | R$_2$ | R$_1$ | X$_1$ | A$_1$ | Y$_1$ | A$_2$ | X$_2$ | y | x | Phase transition temperature (°C) |
|---|---|---|---|---|---|---|---|---|---|---|
| 26 | C$_8$H$_{17}$— | C$_5$H$_{11}$— | —O— | ⬡ | —OC=O | ⬡ | —O— | 3 | 0 | Sm2 $\underset{-1.9}{\overset{2.0}{\rightleftarrows}}$ Cryst. $\underset{-17.5}{\overset{6.2}{\rightleftarrows}}$ SmC* $\underset{5.2}{\overset{14.3}{\rightleftarrows}}$ Ch $\underset{13.7}{\overset{}{\rightleftarrows}}$ Iso. |
| 27 | C$_9$H$_{19}$— | C$_5$H$_{11}$— | — | N⬡N (pyrazine) | — | — | —O— | 3 | 0 | Cryst. $\overset{23.3}{\underset{-22.7}{\rightleftarrows}}$ Sm2 $\overset{23.3}{\underset{11.0}{\rightleftarrows}}$ SmA → Iso. |
| 28 | C$_8$H$_{17}$— | C$_2$H$_5$— | —O— | ⬡ | —CO=O | ⬡ | +CH$_2\overline{)_2}$CO=O | 1 | 0 | SmA $\underset{-1.7}{\overset{16.1}{\rightleftarrows}}$ Iso. |
| 29 | C$_{10}$H$_{21}$— | C$_5$H$_{11}$— | — | N⬡N (pyrazine) | — | — | —O— | 5 | 0 | Cryst. $\underset{22.7}{\overset{30.4}{\rightleftarrows}}$ Sm2 $\underset{33.3}{\overset{35.5}{\rightleftarrows}}$ SmC* $\underset{39.8}{\overset{41.4}{\rightleftarrows}}$ Iso. |
| 30 | C$_{12}$H$_{25}$— | C$_5$H$_{11}$— | —O— | ⬡ | —CO=O | ⬡ | —O— | 3 | 0 | Sm4 $\underset{9.1}{\overset{19.2}{\rightleftarrows}}$ Cryst. $\underset{5.9}{\overset{}{\rightleftarrows}}$ Sm3 $\underset{15.9}{\overset{23.1}{\rightleftarrows}}$ SmC* $\underset{35.3}{\overset{38.4}{\rightleftarrows}}$ SmA $\underset{39.7}{\overset{41.3}{\rightleftarrows}}$ Iso. |

TABLE 2

$$R_3-X_3-\left[\underset{a}{\text{A}}\right]-\left[\underset{b}{\text{B}}\right]-\left[\underset{c}{\text{C}}\right]-\left[Y_2-\underset{d}{\text{phenyl}}\right]_e-X_4-\underset{*}{CH_2CH}-R_4$$
with F substituent on the chiral carbon (3)

| Compound | $R_3$ | $R_4$ | $X_3$ | a | A | b | B | c | C | $Y_2$ | d | e | $X_4$ | Phase Transition temperature (°C) |
|---|---|---|---|---|---|---|---|---|---|---|---|---|---|---|
| 31 | $C_8H_{17}-$ | $C_6H_{13}-$ | $-O-$ | 2 | phenyl | 0 | — | 0 | — | — | — | 0 | $-COO-$ | Cryst. $\underset{85.2}{\overset{95.2}{\rightleftarrows}}$ Iso. |
| 32 | $C_{10}H_{21}-$ | $C_6H_{13}-$ | $-O-$ | 2 | phenyl | 0 | — | 0 | — | — | — | 0 | $-COO-$ | Cryst. $\underset{85.0}{\overset{92.3}{\rightleftarrows}}$ Iso. |
| 33 | $C_8H_{17}-$ | $C_5H_{11}-$ | — | 1 | pyrimidine | 1 | phenyl | 0 | — | — | — | 0 | $-O-$ | Cryst. $\underset{-3.4}{\overset{25.4}{\rightleftarrows}}$ SmA $\underset{23.0}{\overset{41.5}{\rightleftarrows}}$ Iso. |
| 34 | $C_8H_{17}-$ | $C_6H_{13}-$ | — | 1 | pyrimidine | 1 | phenyl | 0 | — | — | — | 0 | $-O-$ | Cryst. $\overset{61.5}{\rightarrow}$ Iso. $\overset{58.5}{\rightarrow}$ SmA $\overset{44.8}{\rightarrow}$ |
| 35 | $C_7H_{15}-$ | $C_8H_{17}-$ | — | 1 | pyrimidine | 1 | phenyl | 0 | — | — | — | 0 | $-COO-$ | Cryst. $\underset{58.6}{\overset{70.3}{\rightleftarrows}}$ Iso. |
| 36 | $C_{10}H_{21}-$ | $C_7H_{15}-$ | $-O-$ | 2 | phenyl | 0 | — | 0 | — | $-COO-$ | — | 1 | $-COO-$ | Cryst. $\overset{105.4}{\rightarrow}$ SmC* $\overset{152.9}{\rightarrow}$ SmA $\underset{151.0}{\overset{178.3}{\rightleftarrows}}$ Iso.; 94.4 → Sm3, 80.4 |
| 37 | $C_8H_{17}-$ | $C_6H_{13}-$ | $-O-$ | 2 | phenyl | 0 | — | 0 | — | $-COO-$ | — | 1 | $-COO-$ | Cryst. $\overset{107.7}{\rightarrow}$ SmC* $\overset{185.3}{\rightarrow}$ SmA $\underset{185.1}{\overset{188.2}{\rightleftarrows}}$ Iso.; 81.1 → Sm3, 70.5 |
| 38 | $C_7H_{15}-$ | $C_8H_{17}-$ | — | 1 | pyrimidine | 0 | — | 0 | — | $-COO-$ | — | 1 | $-O-$ | Cryst. $\underset{61.3}{\overset{88.1}{\rightleftarrows}}$ SmA $\underset{139.7}{\overset{141.8}{\rightleftarrows}}$ Ch $\underset{153.5}{\overset{155.7}{\rightleftarrows}}$ Iso. |

TABLE 2-continued $$R_3-X_3\left[\underset{a}{\underset{A}{\bigcirc}}\right]_b\left[\underset{\overline{h}}{\underset{B}{\bigcirc}}-\underset{\overline{h}}{\underset{C}{\bigcirc}}\right]_c\left[Y_2\right]_e\left[\underset{d}{\underset{\bigcirc}{\bigcirc}}\right]_d X_4-CH_2\overset{*}{C}H-R_4$$
$$\phantom{xxxxxxxxxxxxxxxxxxxxxxxxxxxxxxxxxxxxxxxxxxxxxxxx}|$$
$$\phantom{xxxxxxxxxxxxxxxxxxxxxxxxxxxxxxxxxxxxxxxxxxxxxxxx}F$$

| Compound | $R_3$ | $R_4$ | $X_3$ | a | A | b | B | c | C | $Y_2$ | e | d | $X_4$ | Phase Transition temperature (°C.) |
|---|---|---|---|---|---|---|---|---|---|---|---|---|---|---|
| 39 | $C_{10}H_{21}-$ | $C_8H_{17}-$ | $-O-$ | 2 | ⌬ | 0 | — | 0 | — | $-CO-O-$ | 1 | 1 | $-O-$ | Cryst. ⇌ 120.4/115.4 SmC* ⇌ 175.0/172.8 SmA ⇌ 191.7/188.9 Iso.; Cryst. ⇌ 103.2 Sm3 |
| 40 | $C_8H_{17}-$ | $C_6H_{13}-$ | $-O-$ | 1 | ⌬ | 0 | — | 0 | — | $-CO-O-$ | 1 | 2 | $-O-$ | Cryst. ⇌ 130.6/109.3 SmC* ⇌ 172.6/169.8 Ch ⇌ 193.2/190.5 Iso. |
| 41 | $C_8H_{17}-$ | $C_8H_{17}-$ | $-O-$ | 1 | ⌬ | 0 | — | 0 | — | $-CO-O-$ | 1 | 1 | $-O-$ | Cryst. ⇌ 70.1/55.5 SmC* ⇌ 76.8/76.2 SmA ⇌ 84.3/82.4 Ch ⇌ 87.1/84.9 Iso. |
| 42 | $C_8H_{17}-$ | $C_8H_{17}-$ | $-O-$ | 1 | ⌬ | 0 | — | 0 | — | $-CO-O-$ | 1 | 1 | $-CO-O-$ | Cryst. ⇌ 64.8/40.2 SmA ⇌ 59.9 Iso. |
| 43 | $C_7H_{15}-$ | $C_8H_{17}-$ | — | 1 | ⌬(H) | 0 | N⌬N | 1 | ⌬ | — | 0 | 0 | $-CO-O-$ | Cryst. ⇌ 71.8/29.1 Iso. |
| 44 | $C_{12}H_{25}-$ | $C_6H_{13}-$ | $-O-$ | 1 | ⌬ | 0 | — | 0 | — | $-CO-O-$ | 1 | 1 | $-O-$ | Cryst. ⇌ 83.6/54.7 SmA ⇌ 92.3/89.6 Iso.; Sm3 ⇌ 83.1/64.2 SmC* |
| 45 | $C_6H_{13}-$ | $C_{12}H_{25}-$ | $-O-$ | 1 | ⌬ | 0 | — | 0 | — | $-CO-O-$ | 1 | 1 | $-O-$ | Cryst. ⇌ 69.1 Ch ⇌ 81.4/74.1 Iso. |

TABLE 2-continued $$R_3-X_3-\left(\underset{a}{\underset{A}{\bigcirc}}\right)_a-\left(\underset{b}{\underset{B}{\bigcirc}}\right)_b-\left(\underset{c}{\underset{C}{\bigcirc}}\right)_c-Y_2-\left(\underset{d}{\bigcirc}\right)_d-X_4-\overset{*}{C}H_2\overset{F}{\underset{|}{CH}}-R_4$$

| Compound | $R_3$ | $R_4$ | $X_3$ | a | A | b | B | c | C | $Y_2$ | e | d | $X_4$ | Phase Transition temperature (°C) |
|---|---|---|---|---|---|---|---|---|---|---|---|---|---|---|
| 46 | $C_8H_{17}-$ | $C_6H_{13}-$ | $-O-$ | 1 | ⬡ | 0 | — | 0 | — | $-\underset{\underset{O}{\parallel}}{C}O-$ | 1 | 2 | $-\underset{\underset{O}{\parallel}}{C}O-$ | Cryst. ⇌ 108.4/97.4 SmC* ⇌ 142.0/140.1 SmA ⇌ 171.2/169.6 Ch ⇌ 173.2/171.7 Iso. ; 109.6 Sm3 |
| 47 | $C_{10}H_{21}-$ | $C_5H_{11}-$ | $-O-$ | 1 | ⬡ | 0 | — | 0 | — | $-\underset{\underset{O}{\parallel}}{C}O-$ | 1 | 1 | $-O-$ | Cryst. ⇌ 78.1/53.2 SmC* ⇌ 64.0 SmA ⇌ 86.8/85.0 Iso. |
| 48 | $C_8H_{17}-$ | $C_6H_{13}-$ | $-O-$ | 1 | ⬡ | 0 | — | 0 | — | $-\underset{\underset{O}{\parallel}}{C}O-$ | 1 | 1 | $-O-$ | Cryst. ⇌ 65.7/54.6 SmC* ⇌ 75.8/73.1 SmA ⇌ 82.5/79.9 Ch ⇌ 88.5/86.1 Iso. |
| 49 | $C_8H_{17}-$ | $C_6H_{13}-$ | $-O-$ | 1 | ⬡ | 0 | — | 0 | — | $-\underset{\underset{O}{\parallel}}{O}C-$ | 1 | 1 | $-O-$ | Cryst. ⇌ 85.3/73.2 SmC* ⇌ 82.2 SmA ⇌ 95.5/94.6 Iso. |
| 50 | $\underset{\underset{*}{}}{CH_3}$ $C_2H_5\overset{*}{C}H(CH_2)_3-$ | $C_8H_{17}-$ | $-O-$ | 1 | ⬡ | 0 | — | 0 | — | $-\underset{\underset{O}{\parallel}}{C}O-$ | 1 | 1 | $-O-$ | Cryst. ⇌ 60.8/40.5 SmC* ⇌ 63.1/62.2 Ch ⇌ 66.4/66.0 Iso. |
| 51 | $\underset{\underset{*}{}}{CH_3}$ $C_2H_5\overset{*}{C}H(CH_2)_3-$ | $C_6H_{13}-$ | $-O-$ | 1 | ⬡ | 0 | — | 0 | — | $-\underset{\underset{O}{\parallel}}{C}O-$ | 1 | 1 | $-O-$ | Cryst. ⇌ 65.0/39.4 SmC* ⇌ 57.9 Ch ⇌ 64.7 Iso. |
| 52 | $C_{10}H_{21}-$ | $C_6H_{13}-$ | $-O-$ | 1 | ⬡ | 0 | — | 0 | — | $-CH=CH-$ $-COO-$ | 1 | 1 | $-\underset{\underset{O}{\parallel}}{C}O-$ | Cryst. ⇌ 84.3/64.2 SmC* ⇌ 92.4/91.5 SmA ⇌ 107.8/106.3 Iso. |

The optically active mesomorphic compound represented by the formula (2) may for example be produced through a process as described below.

A compound represented by the following formula (6), as a starting material:

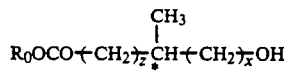
(6)

(wherein $R_0$ denotes a lower alkyl group; C* denotes an asymmetric carbon atom; x and z are 0 or 1 provided that z is 0 or 1 when x=0, and z=0 when x=1) may be synthesized into an optically active alcohol or optically active carboxylic acid represented by the following formula (7):

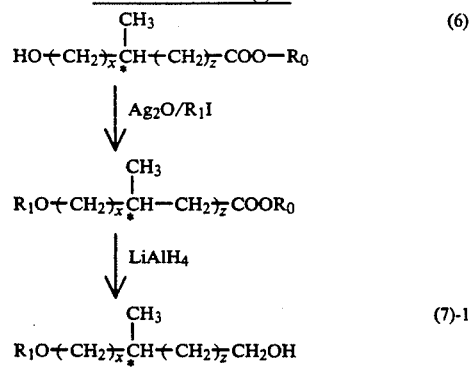

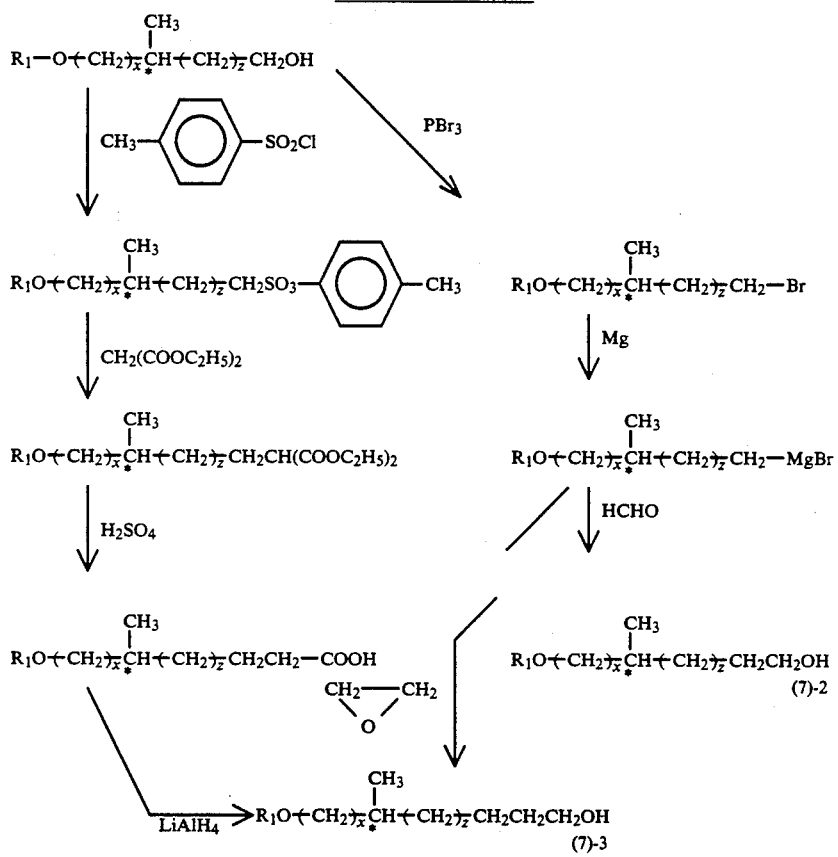

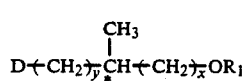
(7)

(wherein $R_1$ denotes a linear or branched alkyl group having 1-18 carbon atoms, y is an integer of 0-8, x is 0 or 1, and D denotes —OH or —COOH) according to the following reaction scheme (1) or (2), or by repeating the reaction scheme (2):

The thus produced optically active alcohol or optically active carboxylic acid may be reacted with a corresponding alcohol or thiol, or a corresponding carboxylic acid, respectively, in a conventional manner to produce an optically active alcohol and an optically active carboxylic acid each having an ether or ester bond represented by the following formulas (8) and (9):

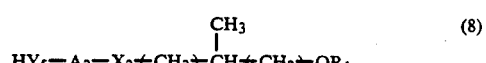
(8)

-continued

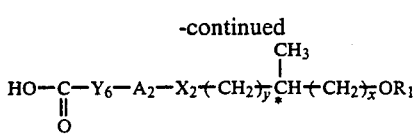
(9)

(wherein $X_2$ denotes a single bond, —O—, —COO—, —OCO—, —CH=CHCOO—, —OCOCH=CH—, or —CH$_2$CH$_2$COO—; $A_2$ denotes a divalent group containing a 6-membered ring and capable of having a substituent (examples of the substituent may include alkyl group, alkoxy group, halogen atom of chlorine, bromine or fluorine, or cyano group, and the divalent group containing a 6-membered ring may for example be

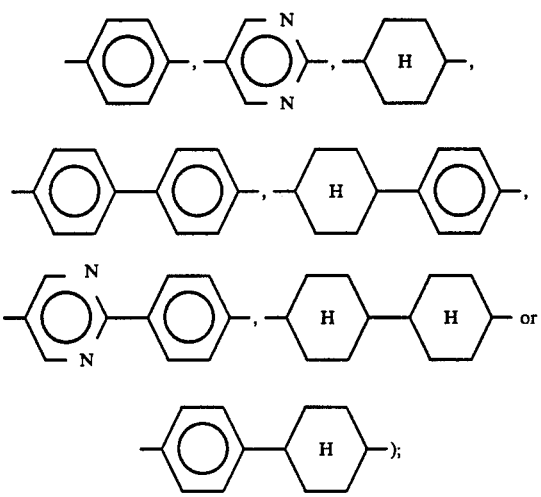

$R_1$ denotes a linear or branched alkyl group having 1-18 carbon atoms; y is an integer of 0-8, x is 0 or 1; $Y_5$ denotes —O— or —S—; $Y_6$ denotes a single bond, —CH=CH— or —CH$_2$CH$_2$—; and C* denotes an asymmetric carbon atom).

The thus obtained optically active compound represented by the formula (7), (8) or (9) may be further reacted with an alcohol, thiol or carboxylic acid represented by the following formula (10) or (11) in a conventional manner:

 (10)

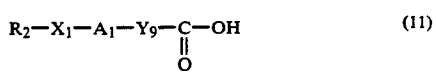 (11)

(wherein $R_2$ denotes a linear or branched alkyl group having 4-16 carbon atoms; $A_1$ denotes a 6-membered ring-containing group capable of having a substituent as described above; $X_1$ denotes a single bond, —O—, —COO—, —OCO—, —CH=CHCO—, or —OCOCH=CH—; $Y_7$ and $Y_9$ denote a single bond, —CH$_2$CH$_2$— or —CH=CH—, and $Y_8$ denotes —O— or —S—); whereby an optically active mesomorphic compound represented by the formula (2) may be obtained.

The optically active fluoroalkane derivative represented by the formula (3) may preferably be produced from optically active intermediates, such as 2-fluoro-1-alkanol, 2-fluoroalkyl p-hydroxybenzoate, 2-fluoroalkyl p-hydroxybiphenylcarboxylate, hydroquinone 2-fluoroalkyl ether, and 4-[4'-(2-fluoroalkyl)-oxyphenyl]-phenol, as disclosed in Japanese Patent Application No. 232886/1985.

From these optically active intermediates, the mesomorphic compounds represented by the formula (3) (particularly those with $Y_2$ being —COO—) may be obtained through the following reaction scheme (the symbols used herein have the same meanings as described above).

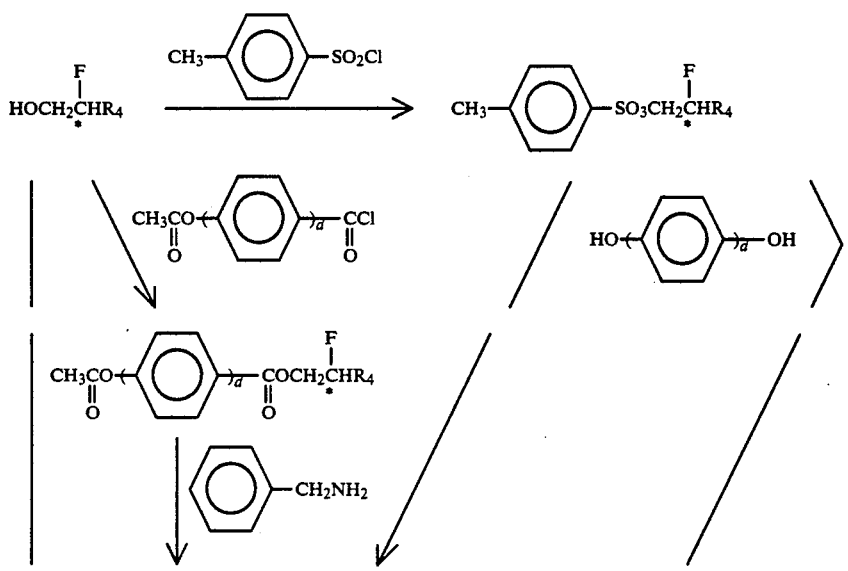

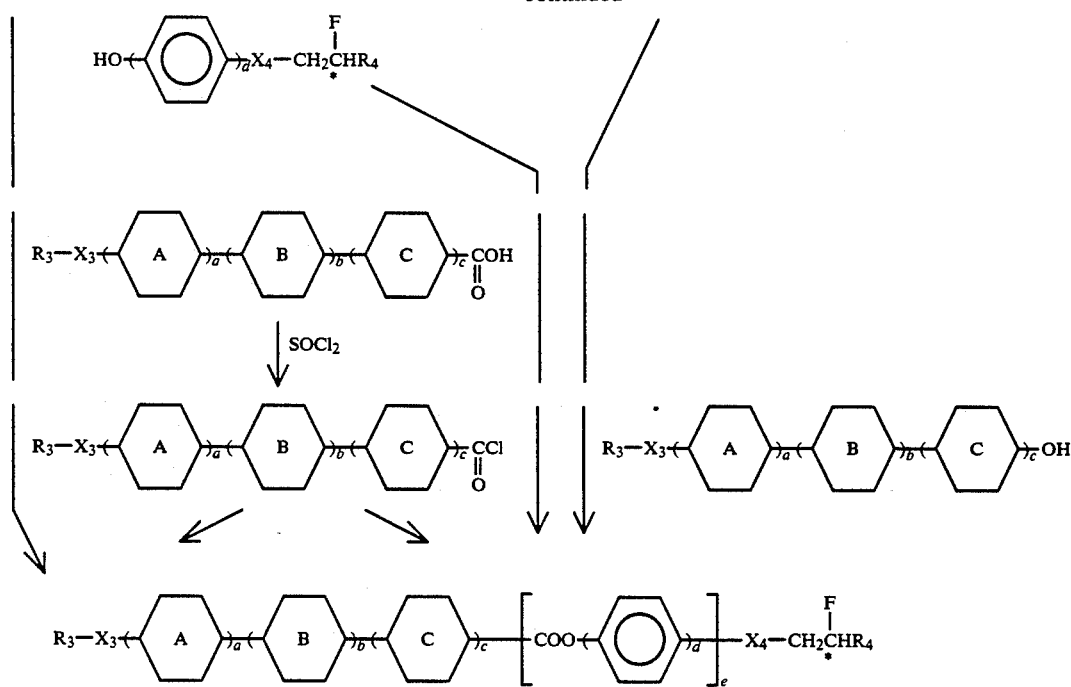

The liquid crystal composition according to the present invention may preferably be prepared by mixing 1-99% of at least one mesomorphic compound having an optically active group represented by the formula (1), preferably one represented by the formula (2), and 99-1% of at least one F-type mesomorphic compound, preferably one represented by the formula (3).

Another preferred class of the liquid crystal composition according to the present invention is one comprising: at least one mesomorphic compound (A) in the form of an ester having an optically active asymmetric carbon atom to which a fluorine atom is directly bonded in its carboxylic acid moiety, and at least one mesomorphic compound (B) in the form of an ester having an optically active asymmetric carbon atom to which a fluorine atom is directly bonded in its alcohol moiety.

The mesomorphic compound (A) having an F-containing optically active group in its carboxylic acid moiety may preferably be one represented by the following formula (4):

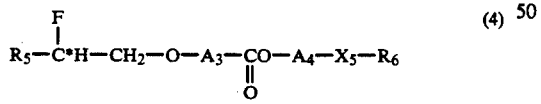
(4)

and the mesomorphic compound (B) having an F-containing optically active group in its alcohol moiety may preferably be one represented by the following formula (5):

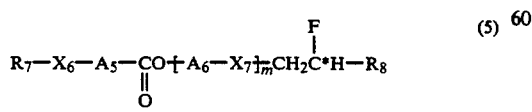
(5)

(wherein the symbols used in the formulas (4) and (5) have the same meanings as defined above).

Representative examples of the above meso-morphic compounds are shown below. First, specific examples of the mesomorphic compound (A) having an F-containing optically active group in its carboxylic acid moiety, preferably those represented by the formula (4), are shown hereinbelow.

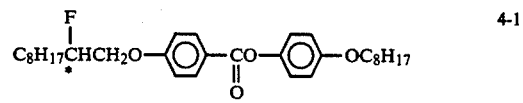
4-1

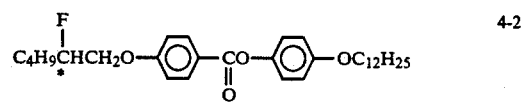
4-2

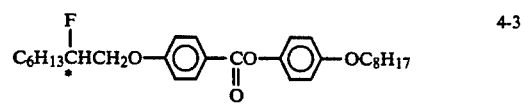
4-3

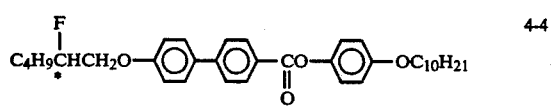
4-4

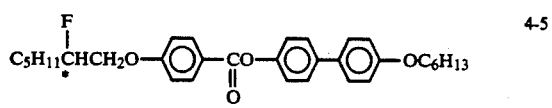
4-5

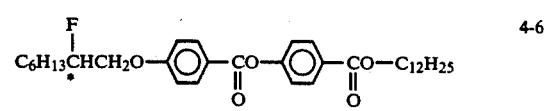
4-6

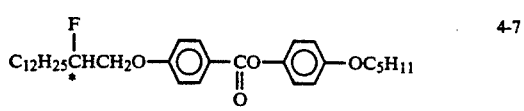
4-7

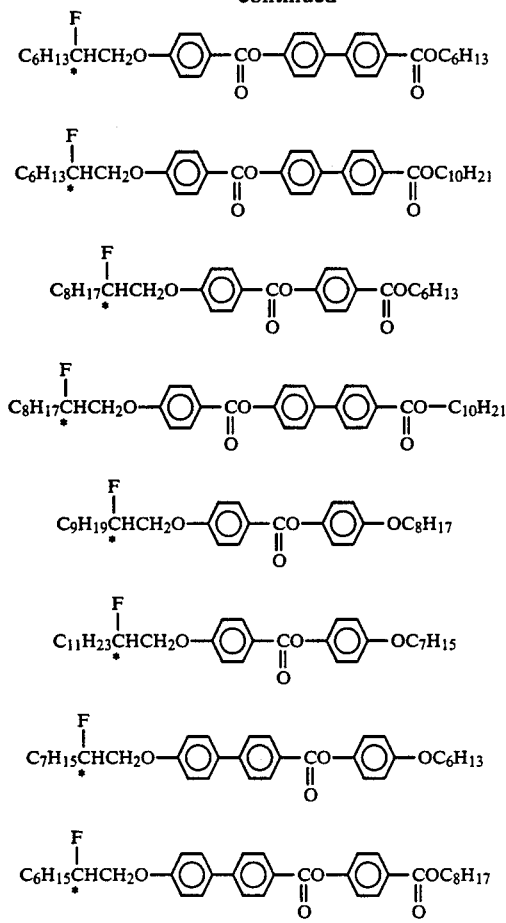

The optically active mesomorphic compounds represented by the formula (4) may preferably be produced through optically active intermediates, such as p-2-fluoroalkoxybenzoic acid, and p'-2-fluoroalkoxybiphenyl-p-carboxylic acid.

For example, the optically active mesomorphic compounds represented by the formula (4) may be synthesized through the following scheme (the symbols used herein have the same meanings as described above):

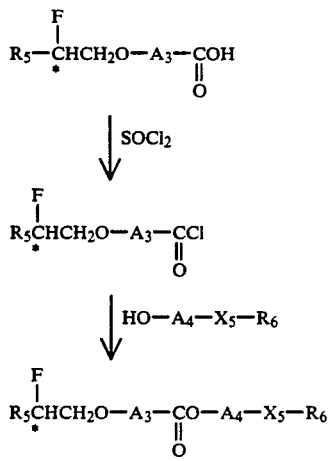

Next, specific examples of the mesomorphic compound (B) having an F-containing optically active group in its alcohol moiety, preferably those represented by the formula (5), are shown below.

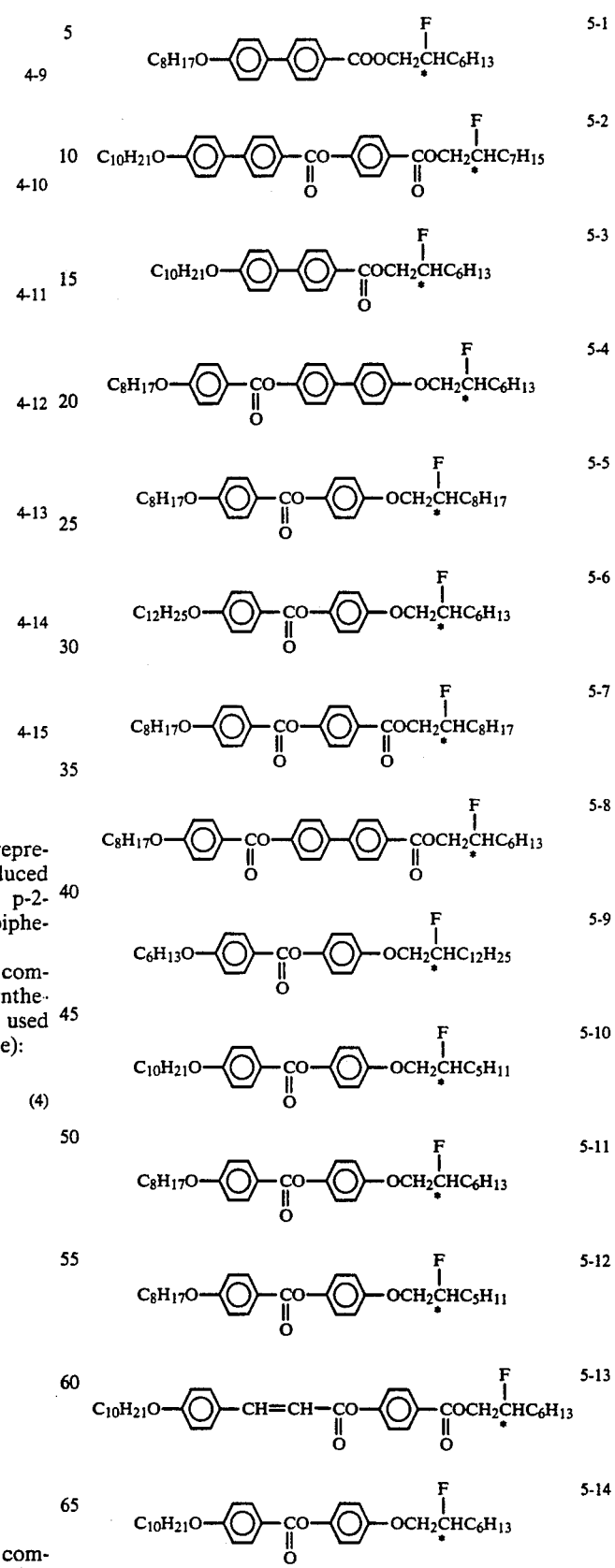

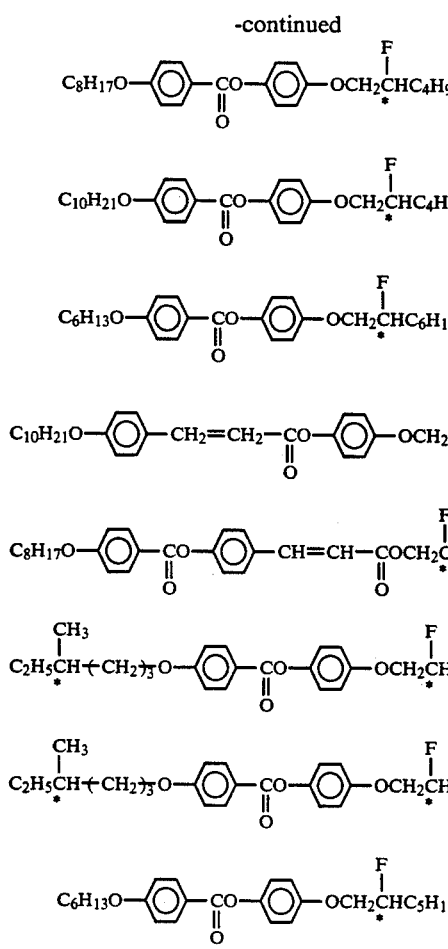

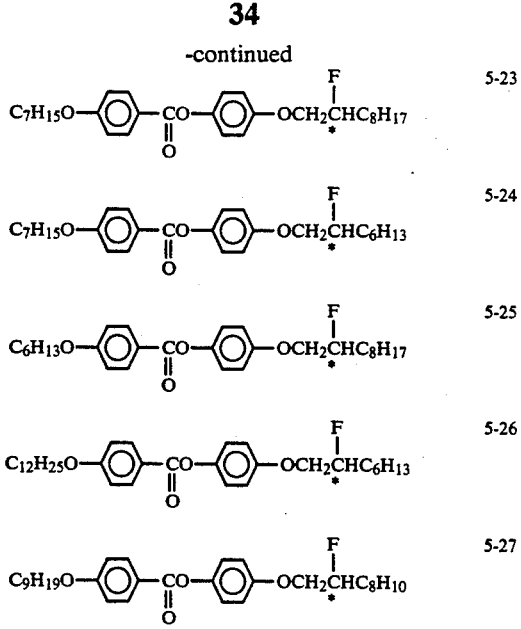

The optically active mesomorphic compound represented by the formula (5) may preferably be produced from optically active intermediates, such as 2-fluoro-1-alkanol, 2-fluoroalkyl p-hydroxybenzoate, 2-fluoroalkyl p-hydroxybiphenylcarboxylate, hydroquinone 2-fluoroalkyl ether, and 4-[4'-(2-fluoroalkyl)-oxyphenyl]-phenol, as disclosed in Japanese Patent Application No. 232886/1985.

From these optically active intermediates, the mesomorphic compounds represented by the formula (3) (particularly those with $Y_2$ being —COO—) may for , example be obtained through the following reaction scheme (the symbols used herein have the same meanings as described above).

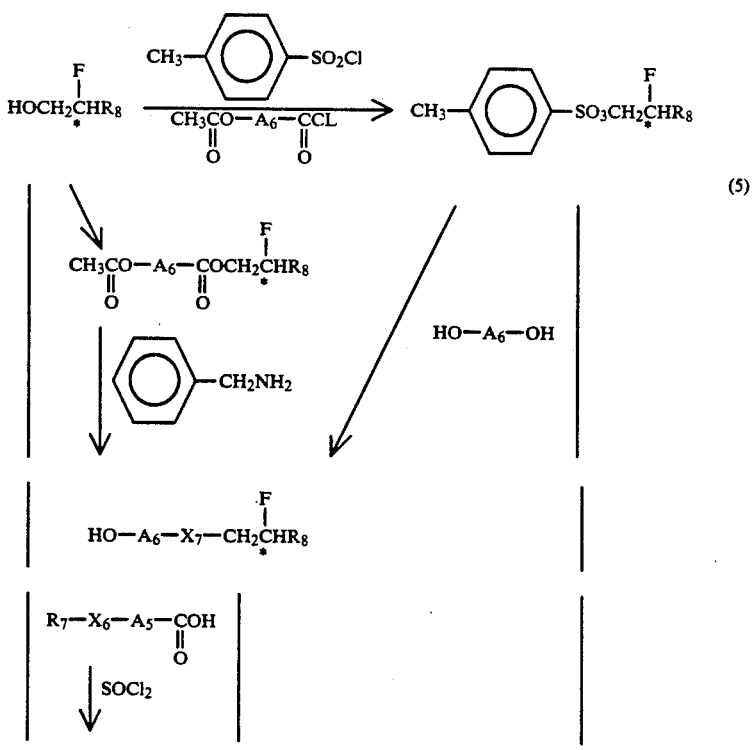

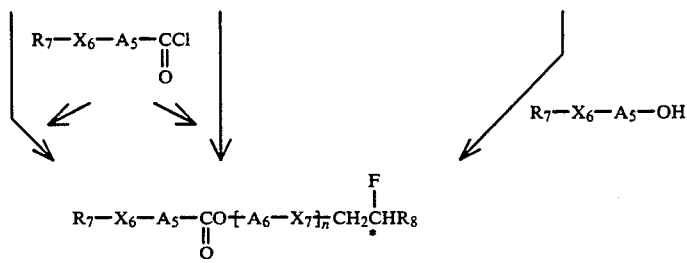

The liquid crystal composition according to the present invention may preferably be prepared by mixing 1-99% of at least one mesomorphic compound (A) having an F-containing optically active group in its carboxylic acid moiety, preferably one represented by the formula (4), and 99-1% of at least one mesomorphic compound (B) having an F-containing optically active group in its alcohol moiety, preferably one represented by the formula (5).

According to the present invention, it has been also confirmed that a class of optically active fluorine atoms represented by the following formula (I) and including some mesomorphic compounds represented by the formula (3) or (4) is effective in itself:

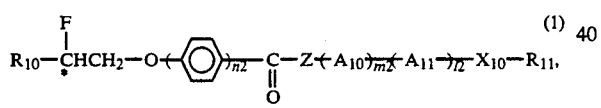
(1)

wherein $R_{10}$ denotes an alkyl group having 1-6 carbon atoms; $C^*$ denotes an asymmetric carbon atoms; $R_{11}$ denotes an alkyl group having 1-6 carbon atoms; Z denotes —O— or —S—; $X_{10}$ denotes a single bond, —O—, or

$A_{10}$ and $A_{11}$ denote a phenylene group

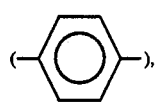

a cyclohexylene group

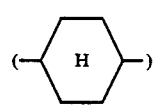

or a pyrimidinylene group

$n_2$ is 1 or 2; l2 and m2 are 0 or a positive integer satisfy the relation l2+m2=1 or 2.

The optically active fluoroalkane derivatives represented by the formula (I) may preferably be produced through optically active intermediates, such as p-2-fluoroalkoxybenzoic acid, and p'-2-fluoroalkoxybiphenyl-p-carboxylic acid.

2-Fluoro-1-alkanols represented by the following formula may be used as the starting materials.

$$R_{10}-C^*H-CH_2-OH$$
(with F on C*)

($R_{10}$ is an alkyl group having 1-6 carbon atoms as defined above.)

Since 2-fluoro-1-alkanol may be easily obtained, for example, by addition of hydrogen fluoride to optically active 1,2-epoxyalkanes.

Then, a p-toluenesulfonic acid ester of an optically active 2-fluoro-1-alkanol as described above or an optically active 2-fluoro-1-bromoalkane derived from the above optically active alcohol, may he reacted with p-hydroxybenzoic acid or p-hydroxybiphenylcarboxylic acid; or may be reacted with p-hydroxyacetophenone, p-hydroxy-p'-acetylbiphenyl, p-cyanophenol, or p-hydroxy-p'-cyanobiphenyl to obtain a ketone or cyanide, which is then oxidized or hydrolyzed; whereby an optically active compound represented by the following formula (II) is obtained.

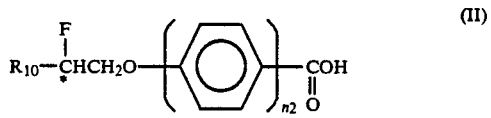
(II)

The above series of reactions may be represented by the following reaction scheme.

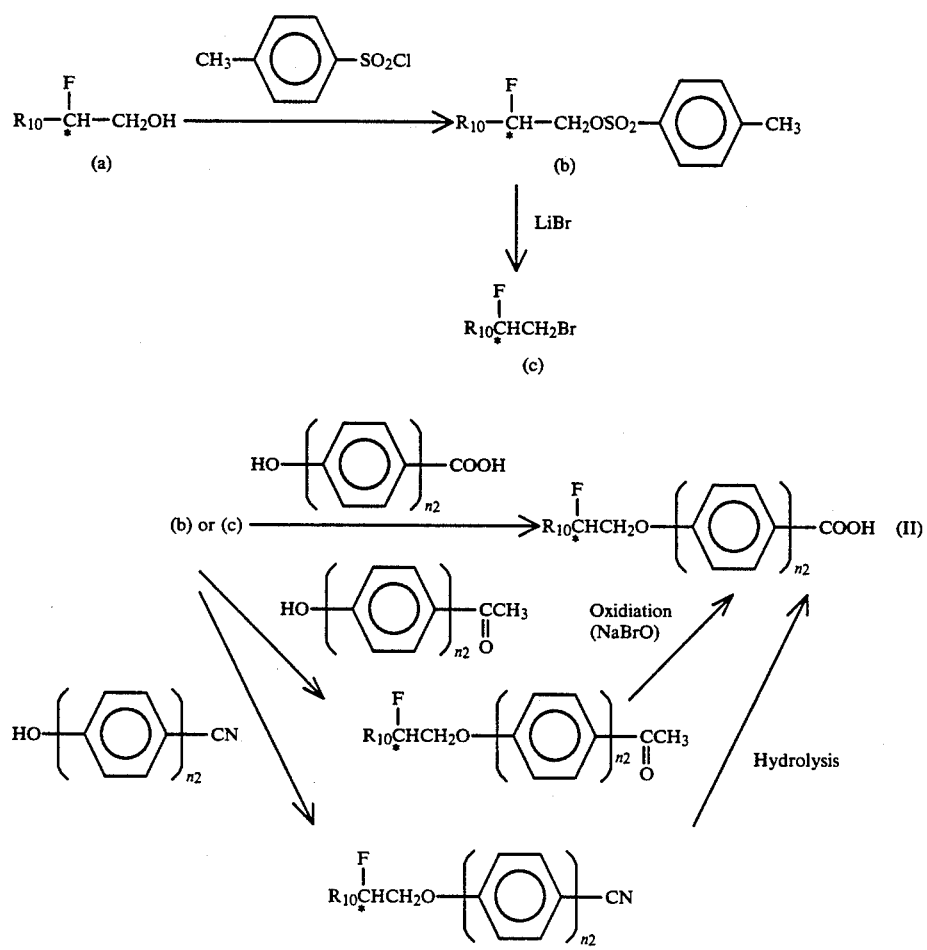

Then, the optically active intermediate represented by the formula (II) may be subjected to reactions along the following scheme to prepare a mesomorphic compound represented by the formula (I):

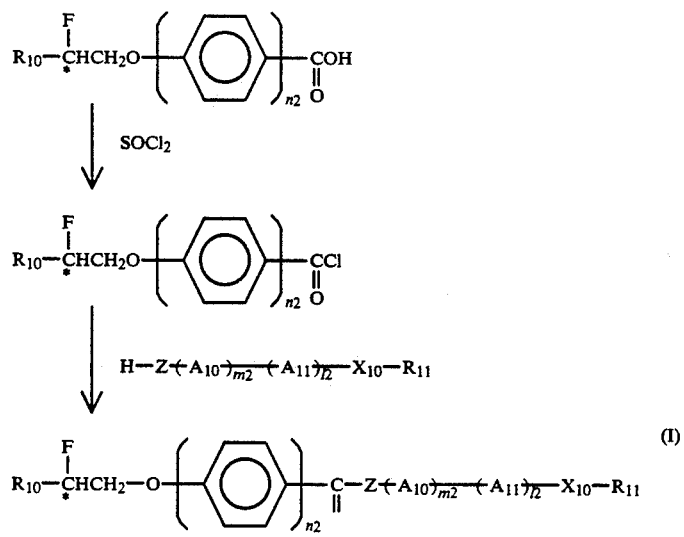

($R_{10}$, $R_{11}$, Z, $A_{10}$, $A_{11}$, $X_{10}$, l2, m2, n2 have the same meanings as described above.)

Hereinbelow, some specific examples of the optically active fluoroalkane derivative synthesized in the above described manner are shown below:

① p'-n-heptyloxyphenyl p-2-fluorohexyloxybenzoate,

② p'-n-hexyloxycarbonylphenyl p-2-fluorohexyloxybenzoate,

③ p'-n-dodecyloxyphenyl p-2-fluoroheptyloxybenzoate,
④ p''-n-heptylphenyl p'-2-fluoroheptyloxybiphenyl-p-carboxylate,
⑤ p'-(p''-n-octyloxyphenyl)-phenyl p-2-fluoroheptyloxybenzoate,
⑥ S-p'-n-dodecyloxyphenyl p-(2-fluoroheptyloxy)-thiobenzoate,
⑦ p'-n-octyloxyphenyl p-2-fluorooctyloxybenzoate,
⑧ 5-n-nonyl-2-[p-(p'-fluorooctyloxybenzoyloxy)phenyl]pyridine,
⑨ p'-(p''-n-octyloxycarbonyl)biphenyl p-2-fluorooctyloxybenzoate,
⑩ trans-p'-(p''-n-octylphenyl) cyclohexyl p-2-fluorooctyloxybenzoate,
⑪ S-p'-n-octylphenyl p-(2-fluorooctyloxy)-thiobenzoate,
⑫ p'-n-decyloxyphenyl p-2-fluorononyloxybenzoate,
⑬ p'-(trans-p''-heptylcyclohexyl) phenyl p-2-fluorononyloxybenzoate,
⑭ p''-n-pentyloxyphenyl p'-2-fluorodecyloxybiphenyl-p-carboxylate,
⑮ p'-n-octyloxyphenyl p-2-fluorodecyloxybenzoate,
⑯ S-p'-n-octyloxyphenyl p-(2-fluorodecyloxy)-thiobenzoate,
⑰ 5-n-octyl-2-[p-(p'-2-fluorodecyloxybenzoyloxy)phenyl]pyrimidine,
⑱ p'-(p''-n-heptyloxycarbonyl) biphenyl p-2-fluorodecyloxybenzoate,
⑲ trans-p'-(trans-p''-n-octylcyclohexyl)cyclohexyl p-2-fluorodecyloxybenzoate,
⑳ S-p'-n-heptyloxyphenyl p-(2-fluoroundecyloxy)-thiobenzoate,
㉑ p-(n-dodecyloxycarbonyl) phenyl p-2-fluoroundecyloxybenzoate,
㉒ p'-n-tetradecyloxyphenyl p-2-fluorododecyloxybenzoate,
㉓ p'-n-nonyloxyphenyl p-2-fluorododecyloxybenzoate,
㉔ S-p'-n-dodecyloxyphenyl p-(2-fluorododecyloxy)-thiobenzoate,
㉕ trans-p''-n-propylcyclohexyl p'-2-fluorododecyloxybiphenyl-p-carboxylate,
㉖ p'-n-butyloxyphenyl p-2-fluorotridecyloxybenzoate,
㉗ p'-(p''-decyloxycarbonyl)biphenyl p-2-fluorotridecyloxybenzoate,
㉘ p'-n-heptyloxyphenyl p-2-fluorotetradecyloxybenzoate,
㉙ p''-n-hexylphenyl p'-2-fluorohexadecyloxybiphenyl-2-carboxylate,
㉚ p'-n-hexyloxyphenyl p-2-fluorohexadecyloxybenzoate.

Another preferred class of the liquid crystal composition according to the present invention contains at least one species of the fluoroalkane derivative represented by the formula (I). For example, the fluoroalkane derivative represented by the formula (I) may be mixed with a ferroelectric liquid crystal selected from those of the formulas <1>—<13> shown below to increase the spontaneous polarization and increase the response speed. In this case, it is preferred to use the fluoroalkane derivative represent by the formula (I) in an amount constituting 0.1–99 wt. %, particularly 1–90 wt. % of the resulting liquid crystal composition.

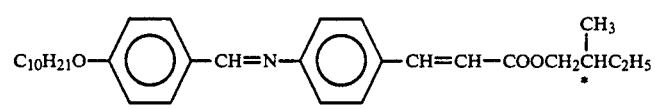

p-decyloxybenzylidene-p'-amino-2-methylbutylcinnamate (DOBAMBC)

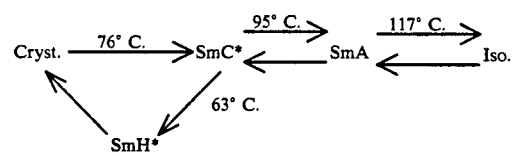

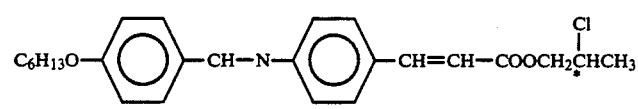

p-hexyloxybenzylidene-p'-amino-2-chloropropylcinnamate (HOBACPC)

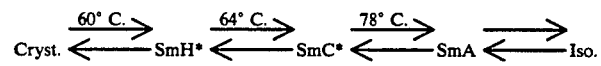

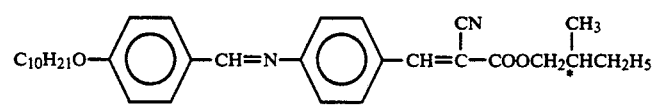

p-decyloxybenzylidene-p'-amino-2-methylbutyl-α-cyanocinnamate (DOBAMBCC)

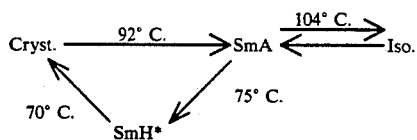
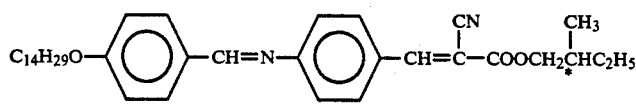
p-tetradecyloxybenzylidene-p'-amino-2-methylbutyl-α-cyanocinnamate
(TDOBAMBCC) <4>
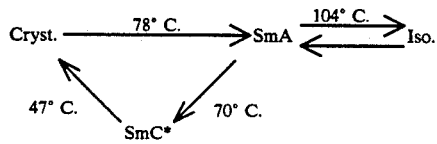
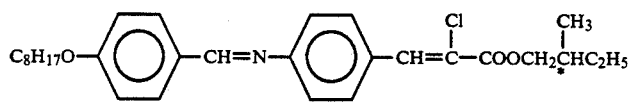
p-octyloxybenzylidene-p'-amino-2-methylbutyl-α-chlorocinnamate
(OOBAMBCC) <5>
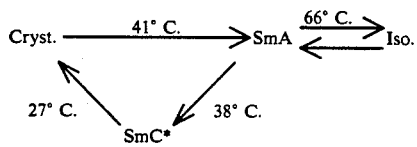
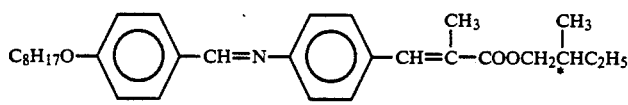
p-octyloxybenzylidene-p'-amino-2-methylbutyl-α-methylcinnamate <6>
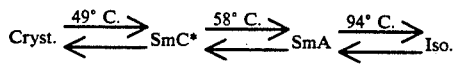
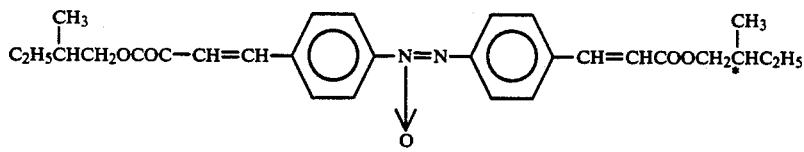
4,4'-azoxycinnamic acid-bis(2-methylbutyl)ester
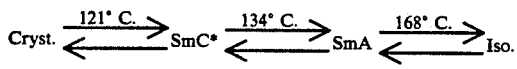
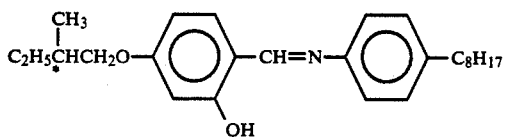
4-O-(2-methylbutyl)resorcylidene-4'-octylaniline <8>

-continued

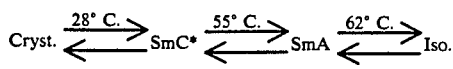

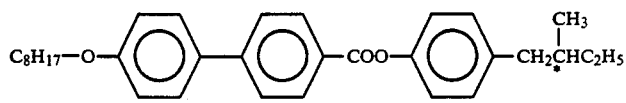

4-(2'-methylbutyl)phenyl-4'-octyloxybiphenyl-4-carboxylate  ⟨9⟩

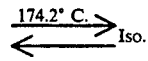

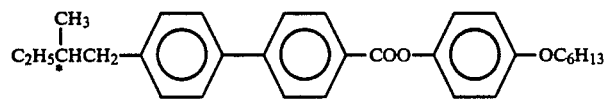

4-hexyloxyphenyl-4-(2''-methylbutyl)biphenyl-4'-carboxylate  ⟨10⟩

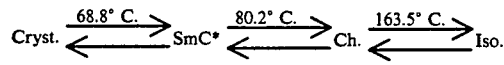

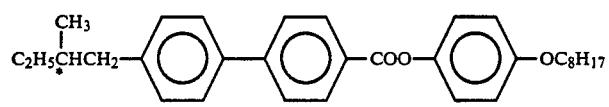

4-octyloxyphenyl-4-(2''-methylbutyl)biphenyl-4-carboxylate  ⟨11⟩

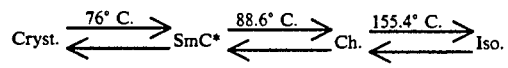

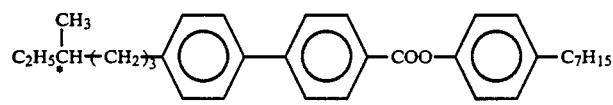

4-hyexyloxyphenyl4-4-(2''-methylbutyl)biphenyl-4'-carboxylate  ⟨12⟩

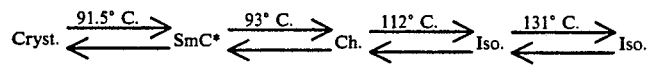

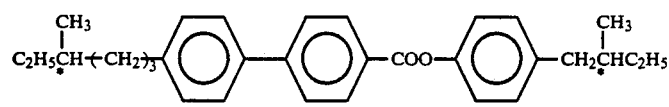

4-(2''-methylbutyl)phenyl-4-(4''-methylhexyl)biphenyl-4'-carboxylate  ⟨13⟩

81.0° C.

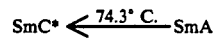

The fluoroalkane derivative represented by the formula (I) may also be mixed with a smectic liquid crystal such as those of the formula ⟨14⟩—⟨18⟩ below which per se are not chiral to provide a composition which may be used as a ferroelectric liquid crystal. In this case, the fluoroalkane derivative represented by the formula (I) may preferably be used in an amount of 0.1–99 wt. %, particularly 1–90 wt. %. The resultant composition may be provided with an increased spontaneous polarization corresponding to the content of a fluoroalkane derivative according to the present invention.

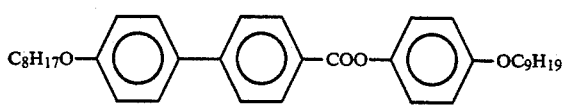

(4-nonyloxyphenyl)-4'-octyloxybiphenyl-4-carboxylate

Cryst. $\xrightleftharpoons[74° C.]{107° C.}$ SmB $\xleftrightarrow{117° C.}$ SmC $\xleftrightarrow{160° C.}$ SmA $\xleftrightarrow{195° C.}$ Iso.  <14>

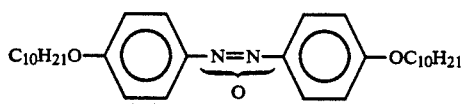

4,4'-decyloxyzaoxybenzene

Cryst. $\xrightarrow{77° C.}$ SmC $\xleftrightarrow{120° C.}$ N $\xleftrightarrow{123° C.}$ Iso.  <15>

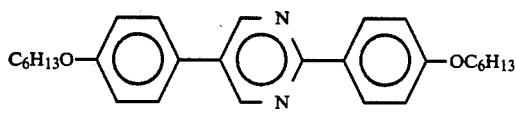

2-(4'-hexyloxyphenyl)-5-(4-hexyloxyphenyl)-pyrimidine

Cryst. $\xrightarrow{120° C.}$ SmC $\xleftrightarrow{189° C.}$ SmA $\xleftrightarrow{216° C.}$ Iso.  <16>

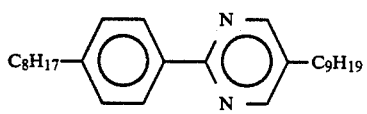

2-(4'-octyloxyphenyl)-5-nonylpyrimidine

Cryst. $\xrightarrow{33° C.}$ SmC $\xleftrightarrow{60° C.}$ SmA $\xleftrightarrow{75° C.}$ Iso.  <17>

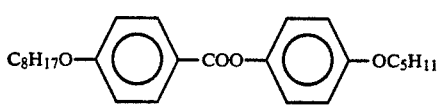

4'-pentyloxyphenyl-4-octylazoxybenzoate

Cryst. $\xrightarrow{58° C.}$ SmC $\xrightarrow{64° C.}$ SmA $\xrightarrow{66° C.}$ N $\xrightarrow{85° C.}$ Iso.  <18>

FIG. 1 is a schematic sectional view of an embodiment of the ferroelectric liquid crystal device for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4, Lead wires 6 are connected to the electrodes so as to apply a driving voltage tot he liquid crystal layer 1 from a power supply 7. Outside the substrates 2, a pair of polarizers 8 are disposed so as to modulate incident light I₀ from a light source 9 in cooperation with the liquid crystal 1 to provide modulated light I.

Each of two glass substrates 2 is coated with a transparent electrode 3 comprising a film of In₂O₃, SnO₂ or ITO (Indium-Tin Oxide). Further thereon, an insulating alignment control layer 4 is formed by rubbing a film of a polymer such as polyimide with gauge or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose regin, melamine resin, urea resin, acrylic resin, or photoresist regin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The inorganic insulating layer may have a thickness of ordinarily 50 Å−1μ, preferably 100 Å−5000 Å, further preferably 500 Å−3000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching specers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer in a thickness of generally 0.5 to 20μ, preferably 1 to 5μ.

The transparent electrodes 3 are connected to the external power supply 7 through the lead wires 6. Further, outside the glass substrates 2, polarizers 8 are applied. The device shown in FIG. 1 is of a transmission type.

Figure 2:
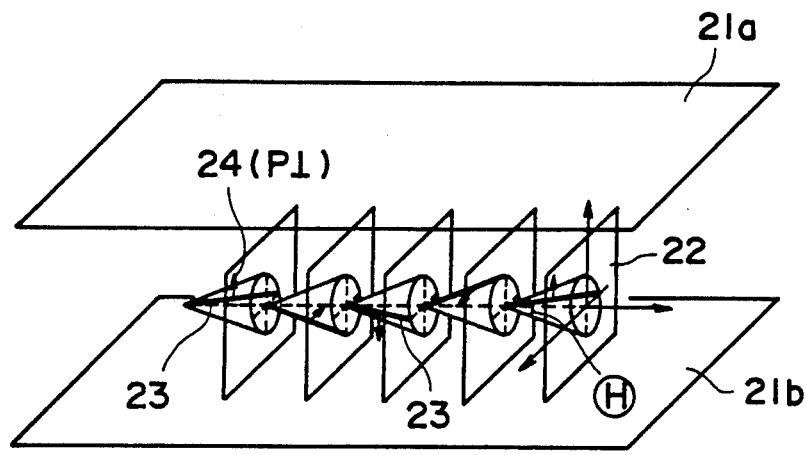
FIGS. 2 and 3 are each a schematic sectional view for illustrating operation of a ferroelectric liquid crystal device.

FIG. 2 is a schematic illustration of a ferro-electric liquid crystal cell (device) for explaining operation thereof. Reference numerals 21a and 21b denote substrates (glass plates) on which a transparent electrode of, e.g., In$_2$O$_3$, SnO$_2$, ITO (Indium Tin Oxide), etc., is disposed, respectively. A liquid crystal of an SmC*-phase (chiral smectic C phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. A half of the apical angle of the helical cone at this time is equal to the tile angle (H) in chiral smectic phase with a helical structure. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
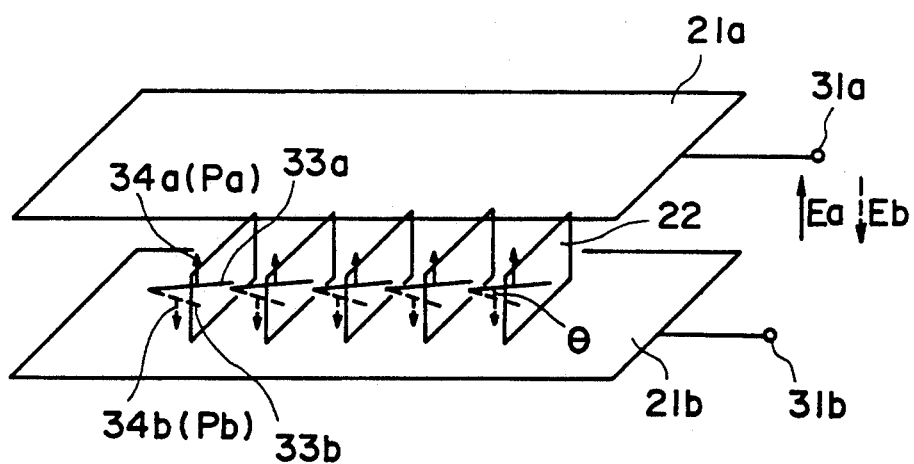

Further, when the liquid crystal cell is made sufficiently thin (e.g., about 1μ), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b. A half of the angle between the liquid crystal molecular axes in the first and second stable states corresponds to a tilt angle θ in a chiral smectic phase with a non-helical structure.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Hereinbelow, the present invention will be explained more specifically with reference to Examples.

The spontaneous polarization values $P_S$ referred to in the Examples were measured according to "Direct Method with Triangular Waves for Measuring Spontaneous Polarization in Ferroelectric Liquid Crystal", as described by K. Miyasato et al (Jap. J. Appl. Phys. 22, No. 10, L 661 (1983)). The polarity of $P_S$ was measured according to the definition of Clark et al (N. A. Clark and S. T. Lagerwall, Ferroelectrics, 59, p. 25 (1984)). Incidentally, a mesomorphic compound not showing a chiral smectic phase by itself was mixed with a mesomorphic compound showing smectic C phase and not having $P_S$ in a proportion of 10:90 to be formed into chiral smectic C phase. Then, the $P_S$ value of the mixture was measured as a 10% value, which was then extrapolated to 100% value, i.e., the estimated $P_S$ value of the sample mesomorphic compound.

EXAMPLE 1

Mesomorphic compound 15 and mesomorphic compound 41 shown in Tables 1 and 2, respectively, described before were mixed in a proportion of 84:16 to obtain a liquid crystal composition.

The liquid crystal composition showed the following phase transition characteristic.

Thus, the liquid crystal composition showed a temperature range of chiral smectic C phase which was expanded to both the higher temperature side and the lower temperature side compared with that of the mesomorphic compound 15 alone, and also retained its SmC* phase relatively stably even at a supercooling temperature.

The spontaneous polarization and response speed of the composition were measured and shown together with those of the mesomorphic compound 15 alone in the following Table 3.

TABLE 3

| | Sample | |
|---|---|---|
| | Compound 15 alone | Composition 15 + 41 (84:16) |
| Spontaneous polarization (25° C.) | 9.5 nc/cm² | 14.3 nc/cm² |
| Response time (35° C.) | 260 μsec | 230 μsec |

The response time was measured by sandwiching a sample liquid crystal material (compound or composition) between a pair of electrode plates coated with rubbed polyimide films to provide a liquid crystal cell having a liquid crystal layer thickness of 2 μm, and applying a peak-to-peak voltage of 20V to the cell, thereby to measure the optical response of the cell under right-angle cross nicols. A time in which a transmittance change of 90% occurred was measured and recorded as the response time.

As is understood from the above results, the mixture liquid crystal according to the present invention showed a broader temperature range for SmC* phase and an improved response speed compared with the single mesomorphic compound because of a large spontaneous polarization of the F-type mesomorphic compound.

EXAMPLE 2

A liquid crystal composition A obtained by mixing the mesomorphic compounds 5, 6 and 10 shown in the Table 1 described before in ratios of 1:1:2 showed the following phase transition characteristic:

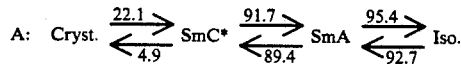

The mesomorphic compounds 5, 6 and 10 showed the following spontaneous polarizations $P_S$ (at a temperature T 10° C. below the upperlimit temperature $T_C$ of the chiral smectic phase) and directions of helical winding direction L (left) or R (right):

| Compound | $P_S$ (at T = $T_C$ − 10) | Winding |
|---|---|---|
| 5 | +21 nC/cm² | left |
| 6 | +15 nC/cm² | left |
| 10 | +20 nC/cm² | left |

On the other hand, a liquid crystal composition B obtained by mixing the mesomorphic compounds 44 and 48 in the Table 2 described before showed the following phase transition characteristic:

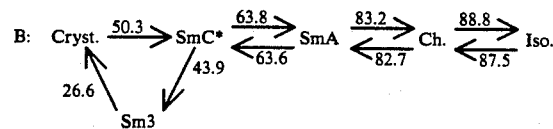

The mesomorphic compounds 44 and 48 showed the following spontaneous polarizations $P_S$ and helical winding directions.

| Compound | $P_S$ (at T = $T_C$ − 10) | Winding |
|---|---|---|
| 44 | −41 nC/cm² | left |
| 48 | −61 nC/cm² | left |

Figure 7:
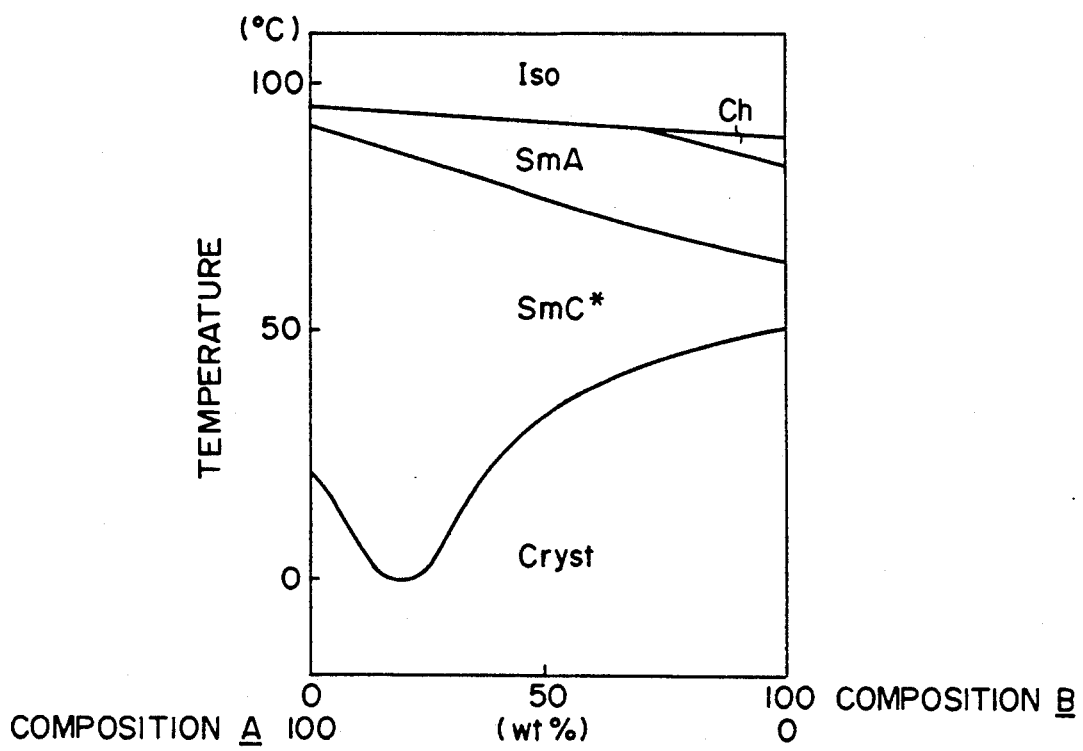
FIG. 7 is a phase diagram showing a change in phase transition temperature due to mixing of a liquid crystal composition A, and a liquid crystal composition B based on Example 2.
Figure 8:
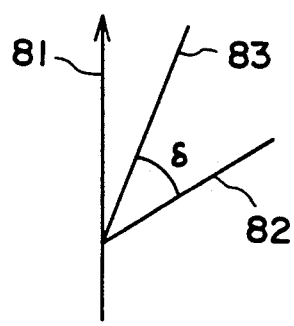
FIG. 8 is a schematic plan view illustrating a twist alignment of liquid crystal molecules along a normal to a substrate.

FIG. 7 is a phase transition diagram of liquid crystal compositions AB obtained by mixing the above two liquid crystal compositions A and B, showing changes in phase transition temperature obtained in the course of temperature increase. As is apparent from FIG. 7, the temperature range for chiral smectic C is enlarged particularly to the lower temperature side around a mixing ratio of A:B=80:20.

By using a composition $A_{80}$–$B_{20}$ (mixture of A:B=80:20) among the liquid crystal compositions AB, a device was prepared in quite the same manner as in Example 1. The device showed a response time of 550 μsec at 25° C. which is faster than 610 μsec at 25° C. of a device using 100% of the composition A.

The liquid crystal device also showed a tilt angle of 15° and a maximum transmittance of 13% under the same measurement conditions as will be explained in Example 11.

EXAMPLE 3

Mesomorphic compounds 1, 4, 10, 15 and 16 shown in Table 1 and mesomorphic compound 41 shown in Table 2 were mixed in ratios shown in the following Table 4 to prepare a liquid crystal composition.

TABLE 4

| Compound | 1 | 4 | 10 | 15 | 16 | 41 |
|---|---|---|---|---|---|---|
| Mixing ratio (%) | 19 | 10 | 30 | 25 | 5 | 11 |

The liquid crystal composition showed the following phase transitions:

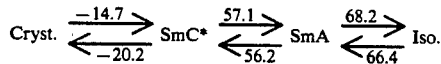

A liquid crystal device prepared by using the above liquid crystal composition in the same manner as in Example 1 showed a response time at 25° C. of 220 μsec.

Thus, this liquid crystal composition showed a temperature region for chiral smectic C phase which was expanded particularly to the low temperature side to form a stable state at room temperature and was improved in response time.

EXAMPLE 4

A liquid crystal composition prepared by mixing mesomorphic compounds 10, 15 and 16 in Table 1 and mesomorphic compounds 33, 44 and 46 in Table 2 in proportions of 35%, 20%, 5%, 5%, 10% and 25%, respectively, was examined with respect to its phase transition characteristic and optical response time, whereby a temperature range for smectic C phase enlarged to the low temperature side and a liquid crystal device with an improved response speed were obtained compared with a case where a single mesomorphic compound was used.

EXAMPLE 5

A liquid crystal composition prepared by mixing mesomorphic compounds 22 and 30 in Table 1 and mesomorphic compounds 33, 44, 46 and 47 in proportions of 15% 5% 10% 15% 35% and 20%, respectively, was confirmed to show similar results as in Example 4.

EXAMPLE 6

Figure 4:
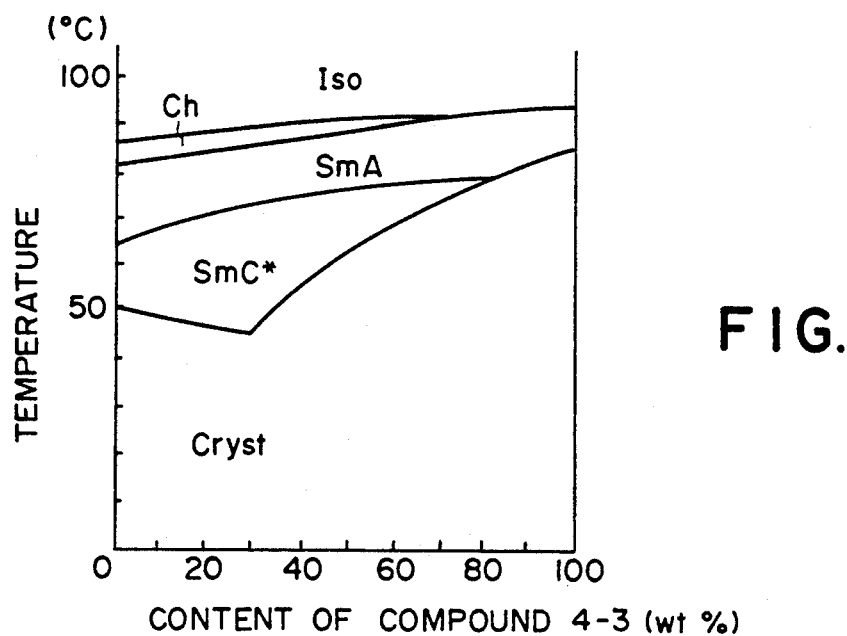
FIG. 4 is a phase diagram showing the change of phase transition temperature depending on the ratio of mixing of a liquid crystal composition 5-a and a mesomorphic compound 4-3 according to Example 6.

A liquid crystal composition which had been obtained by mixing mesomorphic compound 5–12 and mesomorphic compound 5–26 in a ratio 3:1 was mixed with mesomorphic compound 4–3 in various ratios. FIG. 4 shows a change in phase transition temperatures of this mixture system versus the mixing ratio.

Incidentally, the mesomorphic compound 4–3 is a monotropic liquid crystal showing the following phase transitions:

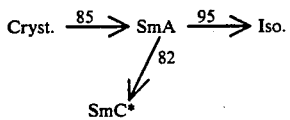

FIG. 4 shows the mixing of the compound 4–7, at 30 wt. % provided a temperature range of SmC* phase of 46° to 72° C. which had been enlarged to both the low temperature side and the high temperature side.

EXAMPLE 7

Two 0.7 ram-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K. K.) in isopropyl alcohol was applied by spinner coating at a speed of 2000 rpm for 15 second and subjected to hot curing treatment at 120° C. for 20 minutes.

Further, each glass plate provided with an ITO film and treated in the above described manner was coated with a 2%-solution of polyimide resin precursor (SP-510, available from Toray K. K.) in dimethylacetoamide by a spinner coater rotating at 2000 rpm for 15 seconds. Thereafter, the coating film was subjected to heat curing at 300° C. for 60 min. to obtain about 700 Å-thick film. The coating film was rubbed with acetate fiber-planted cloth. The thus treated two glass plates were washed with isopropyl alcohol. After alumina beads with an average particle size of 1.5 μm were dispersed on one of the glass plates, the two glass plates were applied to each other with a bonding sealing agent (Lixon Bond available from Chisso K. K.) so that their rubbed directions were parallel to each other and heated at 100° C. for 60 minutes to form a blank cell. The cell gap was found to be about 1.6 μm as measured by a Berck compensator.

Then, the liquid crystal composition of Example 6 containing 30 wt. % of compound 4–3 was heated into an isotropic liquid, and injected into the above prepared cell under vacuum and, after sealing, was gradually cooled at a rate of 0.5° C./hour to 65° C. At that temperature, the cell was observed through a pair of cross nicol polarizers and a microscope, whereby the formation of a monodomain of SmC* phase with a non-helical structure was confirmed.

Figure 5:
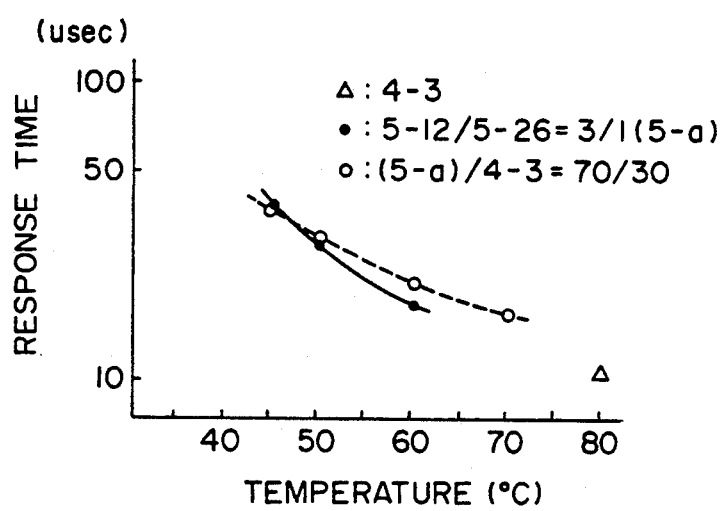
FIG. 5 is graph showing the response speeds of the mesomorphic compound 4-3, the liquid crystal composition 5-a, and a mixture of the mesomorphic compound 4-3 and the liquid crystal composition 5-a at various temperatures according to Example 7.

Then, the optical response time (time from voltage application until the transmittance change reaches 90% of the maximum) was measured under the application of a peak-to-peak voltage of 10V in combination with right-angle cross-nicol polarizers. For comparison, the response times of the liquid crystal composition 5-a and the mesomorphic compound 4–3 were also measured. The results are shown in FIG. 5. It is understood from the figure that the mixture liquid crystal composition according to the present invention has been improved in temperature dependency of response speed.

EXAMPLE 8

A liquid crystal composition (4-a) was prepared by mixing ester-type mesomorphic compounds having a optically active asymmetric carbon atom in their carboxylic acid moiety in the ratios shown below. A liquid crystal composition (5-b) was also prepared by mixing ester-type mesomorphic compounds having an optically active asymmetric carbon atom in their alcohol moiety in the following ratios.

Liquid Crystal Composition (4-a)
4–3/4–6/4–8 = 8/1/1 (wt. ratio)
Liquid Crystal Composition (5-b)
5–5/5–12/5–13/5–27 = 2/4/1/2 (wt. ratio)

The resultant liquid crystal compositions 4-a and 5-b were mixed in a ratio of 1:3 to prepare a liquid crystal composition C. A device was prepared by using the composition C and subjected to measurement of response time in the same manner as in Example 7. The results are shown below together with the results obtained by using the liquid crystal compositions 4-a and 5-b.

|  | 55° C. | 60° C. | 65° C. | 70° C. | 75° C. |
|---|---|---|---|---|---|
| Composition 4-a | — | — | — | — | 20 μsec |
| Composition 5-b | — | 35 μsec | — | 20 μsec | 18 μsec |
| Composition C | 30 μsec | — | 23 μsec | 20 μsec | — |

Figure 6:
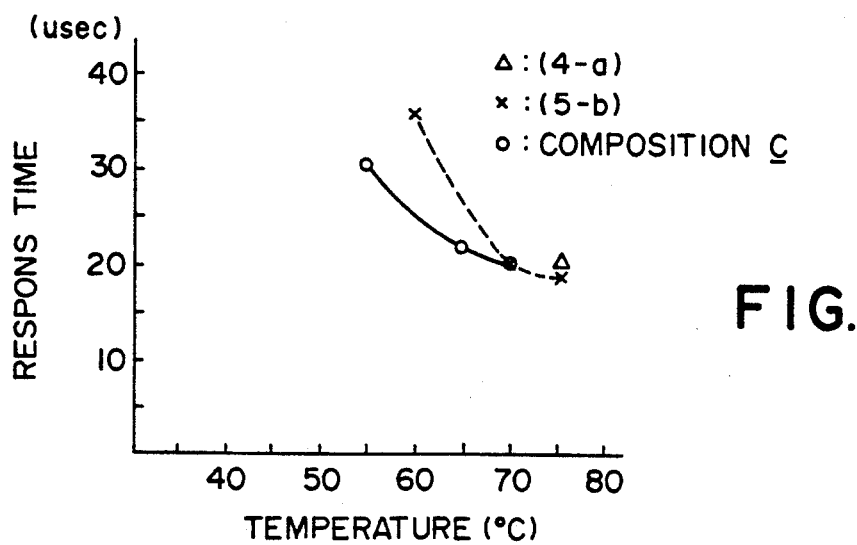
FIG. 6 is a graph showing the dependency of response speeds on temperature based on the results of Example 8.

The above results are shown in FIG. 6.

Then, the device containing the liquid crystal composition C was subjected to driving at 60° C. by application of driving voltages of ±10V and a pulse duration of 50 μsec, whereby good switching was accomplished at a contrast of 17.

As is understood from the above results, the mixture liquid crystal composition according to the present invention provided an improved responsive characteristic at a low temperature and a good display characteristic.

EXAMPLE 9

A liquid crystal composition D was prepared by mixing a liquid crystal composition 4-b [mixture of 4–3/-4–5 = 3/1 (wt. ratio)] and a liquid crystal composition 5-c [mixture of 5–5/5–10 = 2/1 (wt. ratio)] in a ratio of 2:3 (wt. ratio). The liquid crystal composition D was formed into a device and subjected to measurement of response time and observation of switching state in the same manner as in Example 7, whereby it was confirmed that the liquid crystal composition D provided an improvement in response characteristic at low temperatures and display characteristic.

EXAMPLE 10

A liquid crystal composition E was prepared by mixing a liquid crystal composition 4-c [mixture of 4–4/-

4-8=½ (wt. ratio)] and a liquid crystal composition 5-d [mixture of 5-4/5-28=¼ (wt. ratio)] in a ratio of 1:4 (wt. ratio). The liquid crystal composition E was formed into a device and subjected to measurement of response time and observation of switching state in the same manner as in Example 7, whereby it was confirmed that the liquid crystal composition E provided an improvement in response characteristic at low temperatures and display characteristic.

EXAMPLE 11

A liquid crystal composition F was prepared by mixing the following mesomorphic compounds in the indicated proportions.

so that their rubbing directions were parallel to each other with 3 μm-bead spacers therebetween.

The above liquid crystal composition F heated to its isotropic phase was injected under vacuum into the thus prepared blank cell and cooled at a rate of 0.5° C./hr. to 30° C. to be aligned. The experiments thereafter were carried out at 30° C.

The cell was found to contain a uniform monodomain free of defects as a result of observation under cross nicols.

Then, the liquid crystal device 1 was rotated relative to right-angle cross nicols to find a position of the lowest transmittance where the cell provided a black color and a position of the largest transmittance where the

[Liquid crystal composition F]

| Compound | wt. % | $P_S$ (nc/cm$^2$) | Winding |
|---|---|---|---|
| $C_7H_{15}O$–⟨⟩–CO–O–⟨⟩–OCH$_2$CHFC$_8$H$_{17}$ | 21 | −75 ($T_C-T = 10°$ C.) | left |
| $C_6H_{13}O$–⟨⟩–CO–O–⟨⟩–OCH$_2$CHFC$_6$H$_{13}$ | 22 | −80 ($T_C-T = 10°$ C.) | left |
| $C_8H_{13}O$–⟨⟩–SC(=O)–⟨⟩–OCH$_2$CHFC$_8$H$_{17}$ | 22 | −66 ($T_C-T = 12°$ C.) | left |
| $C_{10}H_{21}$–(pyrimidine)–⟨⟩–OCH$_2$CHFC$_8$H$_{17}$ | 5 | −56 ($T_C-T = 8°$ C.) | left |
| $C_{10}H_{21}$–(pyrimidine)–⟨⟩–OCH$_2$CHFC$_6$H$_{13}$ | 10 | −53 ($T_C-T = 7°$ C.) | left |
| $C_{12}H_{25}O$–⟨⟩–CO–O–⟨⟩–COCH$_2$CHFC$_6$H$_{13}$ | 20 | +40 ($T_C-T = 7°$ C.) | right |

A liquid crystal device 1 with a liquid crystal layer thickness of about 3 μm as prepared by using the above liquid crystal composition F.

More specifically, the 3 μm-cell was prepared by using two 0.7 mm thick glass plates each provided with a 1000 Å-thick ITO electrode film coated with 200 Å-thick polyimide film subjected to rubbing as a uniaxial orientation treatment and disposing the glass plates cell provided a yellow color. Thus, it was found that the cell had bistable states of black and yellow states providing a very high contrast. The tilt angle was measured to be 22°.

Then, a liquid crystal device 2 with a liquid crystal layer thickness of 3 μm was prepared in the same manner as above except for using the following liquid crystal composition G having a spontaneous polarization $P_S$ of 1.1 nC/cm$^2$ as a composition.

Composition G

| Compound | Winding | (wt. %) | $P_S$ (nC/cm$^2$) $T_C-T = 15°$ C. |
|---|---|---|---|
| $C_8H_{17}O$–⟨⟩–CO–⟨⟩–OCH$_2$CH(CH$_3$)C$_2$H$_5$ | left | 80% | −2.4 |

-continued

Composition G

| Compound | | Winding | (wt. %) | $P_S$ (nC/cm²) $T_C - T = 15°$ C. |
|---|---|---|---|---|
| 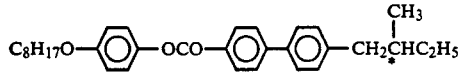 | | right | 20% | +1.0 |

The liquid crystal composition G provided bistable states of blue and yellow with a low contrast therebetween in SmC* phase.

More specifically, when a pulse electric field was applied to the liquid crystal device 2 to provide the liquid crystal molecules with one stable orientation state and the cell was rotated relative to cross nicols to find a position of the lowest transmittance. However, the lowest transmittance state provided not black color but blue color. Black color would have been obtained if the liquid crystal molecules were uniformly aligned in one direction and in parallel with the substrate surfaces.

We considered that the blue color arised from a twist alignment of liquid crystal molecules with respect to a normal to the substrates and further continued experiments. The twist alignment state could be detected whether or not a darker state could be obtained by deviating the relative positions of the polarizer on the light source side and the analyzer on the viewer side from the right angle positions.

As viewed from the viewer side, a clockwise rotation is taken as "positive" and an anti-clockwise rotation is taken as negative. When the analyzer was rotated by 10°-13° in the negative direction from the right-angle cross nicol position, and the cell was rotated, a darkest state was obtained. The same darkest state was obtained also when the polarizer was rotated by 10°-13° in the positive direction from the right-angle cross nicol position. As a result, it was found that the liquid crystal molecules in the device 2 formed a twist alignment in the position direction and the longer axes of liquid crystal molecules adjacent to the upper and lower substrates were twisted at a twist angle δ of 10°-13° from each other. The tilt angle θ was measured to be 6° with the rubbing axis as the center.

As described above, it was found that the liquid crystal device 1 obtained by using the liquid crystal composition F comprising a mesomorphic compound with a negative $P_S$ of below $-10$ nC/cm² showing a negative helical winding and a mesomorphic compound with a positive $P_S$ of above 10 nC/cm² showing a positive helical winding removed such a twist alignment and provided a remarkably improved contrast compared with the liquid crystal device 2 wherein a twist alignment was involved.

EXAMPLE 12

Three cells were prepared in the same manner as in Example 11 except that the cell thickness (spacing between the substrates) was changed to 5 μm, 10 μm and 20 μm, respectively, and the liquid crystal composition F was charged into the respective cells to prepare liquid crystal devices 3-5.

These devices were subjected to voltage application while being observed through a microscope.

The results of observation with respect to tilt angle θ, and colors of darkest state and bright state are shown below.

| | Tilt angle θ | Color Darkest state | Color Brightest state |
|---|---|---|---|
| Liquid crystal device 3 | 22° | black | blue |
| Liquid crystal device 4 | 22° | black | white |
| Liquid crystal device 5 | 20° | black | white |

As shown above, the liquid crystal devices 3-5 using the liquid crystal composition F were free of twist alignment and showed a good contrast. When the cell thickness was increased to 10 μm or above, the brightest state became white and the improvement in contrast became particularly remarkable.

EXAMPLE 13

A liquid crystal composition H was prepared by mixing the following mesomorphic compounds in the indicated proportions.

[Liquid crystal composition H]

| | wt. % | $P_s$ (nC/cm²) | Winding |
|---|---|---|---|
| 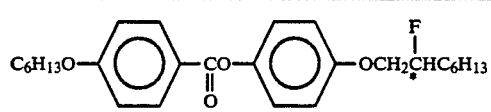 | 15% | $-80$ ($T_C - T = 10°$ C.) | left |
| 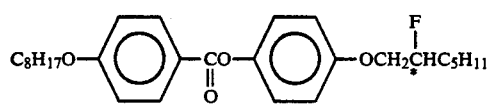 | 15% | $-63$ ($T_C - T = 6°$ C.) | left |
| 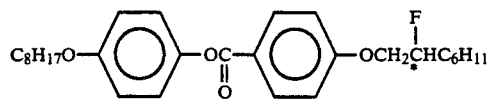 | 5% | $-13$ ($T_C - T = 7°$ C.) | left |

-continued

[Liquid crystal composition H]

| Structure | wt. % | $P_S$ (nC/cm²) | Winding |
|---|---|---|---|
|  $C_6H_{13}O$—⬡—SC(O)—⬡—$OCH_2\overset{*}{C}H(F)C_8H_{17}$ | 10% | −66 ($T_C − T = 12°$ C.) | left |
| $C_{10}H_{21}$—(N-pyridine)—⬡—$OCH_2\overset{*}{C}H(F)C_8H_{17}$ | 6% | −56 ($T_C − T = 7°$ C.) | left |
| $C_{12}H_{25}$—(N-pyridine)—⬡—$OCH_2\overset{*}{C}H(F)C_6H_{13}$ | 8% | −53 ($T_C − T = 8°$ C.) | left |
| $C_{10}H_{21}OC(O)$—⬡—⬡—$OC(O)$—⬡—$OCH_2\overset{*}{C}H(CH_3)OC_5H_{11}$ | 14% | −20 ($T_C − T = 10°$ C.) | right |
| $C_{12}H_{25}O$—⬡—$CO(O)$—⬡—$COCH_2\overset{*}{C}H(F)C_6H_{13}$ | 10% | −39 ($T_C − T = 7°$ C.) | right |
| $C_{13}H_{27}O$—⬡—$CO(O)$—⬡—$COCH_2\overset{*}{C}H(F)C_6H_{13}$ | 12% | +33 ($T_C − T = 5°$ C.) | right |
| $C_8H_{17}O$—⬡—$CO(O)$—⬡—⬡—$COCH_2\overset{*}{C}H(F)C_6H_{13}$ | 4% | 15 ($T_C − T = 15°$ C.) | right |

A cell was prepared in the same manner as in Example 11 except for changing the cell thickness to 1.2 μm, and filled with the liquid crystal composition H to prepare a liquid crystal device 6.

As a result of observation under cross nicols, the device was found to contain a uniform monodomain free of defects and contain bistable states of white and black with a high contrast therebetween.

The liquid crystal device 6 was observed through a microscope while being subjected voltage application as in Example 11, whereby the tilt angle was measured to be 18°. Further, a high transmittance of 16% was obtained.

When the device was subjected to measurement of threshold characteristics under application of pulse electric fields, the threshold voltages were measured to be 6V at 500 μsec, and 1.3V at 100 msec while showing good threshold characteristics.

EXAMPLE 14

A liquid crystal composition I was prepared by mixing the following mesomorphic compounds in the indicated proportions.

[Liquid crystal composition I]

| Structure | Winding | wt. % | $P_S$ (nC/cm²) |
|---|---|---|---|
| $C_{10}H_{21}OC(O)$—⬡—⬡—$OC(O)$—⬡—$OCH_2\overset{*}{C}H(CH_3)OC_5H_{11}$ | left | 3% | +20 ($T_C − T = 10°$ C.) |
| $C_{12}H_{25}O$—⬡—$CS(O)$—⬡—$OCH_2\overset{*}{C}H(CH_3)OC_8H_{17}$ | left | 3% | +10 ($T_C − T = 10°$ C.) |

-continued

| [Liquid crystal composition I] | Winding | wt. % | $P_S$ (nC/cm$^2$) |
|---|---|---|---|
| 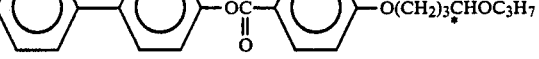 | right | 6% | $-23$ ($T_C - T = 10°$ C.) |
| 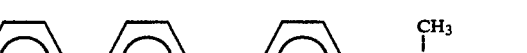 | right | 3% | $-31$ ($T_C - T = 8°$ C.) |
| 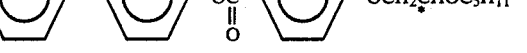 | left | 15% | $-80$ ($T_C - T = 10°$ C.) |
|  | left | 15% | $-63$ ($T_C - T = 12°$ C.) |
| 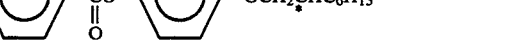 | left | 10% | $-65$ ($T_C - T = 12°$ C.) |
|  | left | 15% | $-17$ ($T_C - T = 8°$ C.) |
| 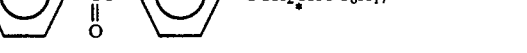 | left | 15% | $-66$ ($T_C - T = 10°$ C.) |
| 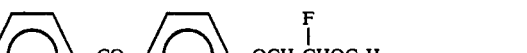 | right | 7% | $+40$ ($T_C - T = 7°$ C.) |
|  | right | 8% | $+42$ ($T_C - T = 7°$ C.) |

A cell was prepared in the same manner as in Example 11 except for changing the cell thickness to 1.2 μm and changing the polyimide film to a polyvinyl alcohol film, and a liquid crystal device 7 was prepared by using the above liquid crystal composition I.

As a result of observation under cross nicols, a uniform monodomain free of defects was found to be formed in the cell. When the cell was rotated relative to the cross nicol polarizers, a darkest state was formed for substantially the whole area.

As a result of measurement in the same manner as in Example 11, the liquid crystal device 7 showed a tilt angle of 15° and a high transmittance of 13%.

EXAMPLE 15

A liquid crystal composition J was prepared by mixing the following mesomorphic compounds in the indicated proportions.

| [Liquid crystal composition J] | Winding | wt. % | $P_S$ (nC/cm$^2$) |
|---|---|---|---|
| <br>(racemic mixture) | — | 63% | — |

-continued

[Liquid crystal composition J]

| Structure | Winding | wt. % | $P_S$ (nC/cm²) |
|---|---|---|---|
| $C_{12}H_{25}$–(pyridine-N,N)–(phenyl)–OCH$_2$CHFC$_6$H$_{13}$ (racemic mixture) | — | 27% | — |
| $C_{12}H_{25}O$–(phenyl)–CO–O–(phenyl)–OCH$_2$C*HFC$_6$H$_{13}$ | left | 8% | −55 ($T_C - T = 15°$ C.) |
| $C_{12}H_{25}O$–(phenyl)–CO–O–(phenyl)–COOCH$_2$C*HFC$_6$H$_{13}$ | right | 2% | +40 ($T_C - T = 7°$ C.) |

A cell was prepared in quite the same manner as in Example 14, and a liquid crystal device 8 was prepared by using the above liquid crystal composition J.

As a result of observation under cross nicols at 35° C., a uniform monodomain free of defects was found to be formed in the cell. The liquid crystal cell in SmC* phase was rotated to a position of the darkest state, where substantially the whole area assumed the darkest state. As a result of measurement in the same manner as in Example 11, the liquid crystal device 8 showed a tilt angle of 20°. Further, the liquid crystal device 8 showed a very large contrast ratio of 50:1.

EXAMPLE 16

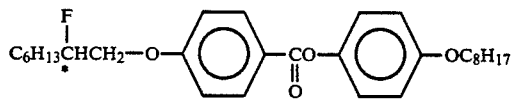

p'-n-octyloxyphenyl p-2-fluorooctyloxybenzoate represented by the above formula was prepared through the following steps (1)-(3).

(1) Synthesis of 2-fluorooctyl bromide 1.51 g (17.4 raM) of LiBr was charged in a 30 ml-round bottomed flask with two ports with grinding fitting, and the interior atmosphere was sufficiently replaced with nitrogen. Dry acetonitrile in an amount of 40 ml was added thereto, and a solution of 3.50 g (11.60 mM) of 2-fluorooctyl p-toluenesulfonate in 4 ml of dry acetonitrile was further added. Thereafter, the system was subjected to about 5 hours of heat refluxing. At this time, as the temperature was raised, the solution became uniform to immediately precipitate a TSO Li salt. After the reaction, the acetonitrile was distilled off, and 10 ml of water and 10 ml of ether were added for extraction. Further, the mixture was subjected to two times of extraction each with 10 ml of ether, and the ether layer was dried with anhydrous sodium sulfate. After the distilling-off of the solvent, 2-fluorooctyl bromide was obtained through distillation in an amount of 2.24 g (yield: 91%, 87°-88° C./28 mm Hg). $[\alpha]_D^{26.4} = -24°$ (C1, CH$_2$Cl$_2$).

(2) Synthesis of p-2-fluorooctyloxybenzoic acid

Into a 100 ml-round bottomed flask, 1.52 g (11 mW) of p-hydroxybenzoic acid in 20 ml of ethanol was added. Thereto, 1.45 g (26 mM) of potassium hydroxide in 5 ml of water was added, and 2.15 g (10 mM) of 2-fluorooctyl bromide in 2 ml of ethanol was added, followed by 25 hours of heat refluxing. Thereafter, a solution of 1.45 g (26 mM) of potassium hydroxide in 3 ml of water was added, followed by 5 hours of heat refluxing. After the completion of the reaction, the system was cooled with ice and neutralized with conc. HCl to precipitate a crystal. The crystal was filtered out, and washed with 50 ml of water to recover 1.00 g (yield: 37%) of p-2-fluorooctyloxybenzoic acid.

(3) Synthesis of p'-n-octyloxyphenyl p-2-fluorooctyloxybenzoate

A vessel was sufficiently dried, and 0.54 g (2.0 mM) of p-2-fluorooctyloxybenzoic acid and 5 ml of thionyl chloride were added and heat-refluxed for 2 hours, followed by removal of unreacted thionyl chloride to recover an acid chloride. Separately, 0.45 g (4.0 mM) of triethylenediamine was dissolved in 5.0 ml of dry benzene and dried for about 30 minutes by adding thereto potassium hydroxide. The solution was charged in a vessel containing p-octyloxyphenol, and the resultant mixture solution was added drop-wise under stirring to the above acid chloride, and thereafter, the system was stirred for 1.5 hours at 50° C. Further, 0.09 g of Nail (purity: 60%, 2.2 mM) was added, and the system was heat-refluxed for 3 hours. After the completion of the reaction, 1N-hydrochloric acid and water were added, and the system was subjected to extraction with benzene. The resultant benzene layer was dried with anhydrous sodium sulfate, and the benzene was distilled off. The remainder was separated by silica gel column chromatography with a mixture of benzene: hexane=2:1 to obtain 0.47 g (50%) of p'-n-octyloxyphenyl p-2-fluorooctyloxybenzoate, which was recrystallized from 4 ml of hexane to obtain 0.40 g (43%).

$[\alpha]_D^{27.2} = -4.2°$ (C1, benzene).

Phase transition temperature:

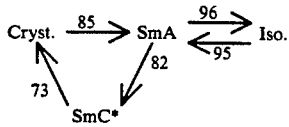

EXAMPLE 17

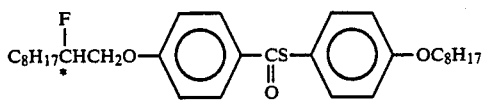

S-p'-octyloxyphenyl p-(2-fluorodecyloxy)-thiobenzoate represented by the above formula was prepared through the following steps (1)–(4).

(1) Synthesis of 2-fluorodecyl p-toluenesulfonate 17 g of 2-fluorodecanol and 60 ml of pyridine were charged into a 300 ml three-necked round bottom flask and cooled to 0° C. to which 24 g of p-toluenesulfonyl chloride was added in 15 min. The system was held at 0° C. for 1 hour and then subjected to reaction for 7 hours while being held below 20° C. Then, the mixture was charged into water and acidified with hydrochloric acid, followed by extraction with dichloromethane. The organic layer was washed with water, dried with magnesium sulfate and then purified by silica gel chromatography with the use of dichloromethane as the eluent to obtain 23 g of 2-fluorodecyl p-toluenesulfonate.

(2) Synthesis of p-(2-fluorodecyloxy)acetophenone 9.2 g of 2-fluorodecyl p-toluenesulfonate obtained in the previous step, 3.8 g of p-hydroxyacetophenone and 10 ml of butanol were charged in a 100 ml-three necked round bottom flask, and a solution of 1.5 g of sodium hydroxide in 10 ml of butanol was added thereto under stirring. After heat-refluxing for 6 hours, the reaction mixture was charged in water, extracted with iropropyl ether, and dried on magnesium sulfate. After distilling off the solvent, the reaction mixture was purified by silica gel column chromatography with the use of a 10:1 mixture solvent of hexane and ethyl acetate as the eluent and recrystallized from hexane to obtain 4.6 g of p-(2-fluorodecyloxy)acetophanone.

(3) Synthesis of p-(2-fluorodecyloxy)benzoic acid

A solution of 11.3 g of sodium hydroxide in 75 ml of water was charged in a 300 ml-three necked flask and cooled to 0° C., and 12.3 g of bromine was added thereto in 15 minutes under stirring, followed by addition of 30 ml of dioxane. The resultant mixture solution was added dropwise in 40 minutes to a solution which was obtained by dissolving 5.2 g of p-(2-fluorodecyloxy) acetophenone in 170 ml of dioxane followed by addition of 10 ml of water, and subjected to reaction for 3.5 hours while being kept below 10° C. Thereafter, the excessive hypobromite was removed by addition of a hydrosulfite aqueous solution, followed by acidification with addition of 6N-hydrochloric acid aqueous solution, and addition of 500 ml of water to precipitate a crystal, which was then recovered by filtration. The crystal was recrystallized from isopropyl ether to obtain 4.1 g of p-(2-fluorodecyloxy)benzoic acid.

IR (cm$^{-1}$): 2950, 2930, 2860, 2670, 2550, 1682, 1608, 1436, 1300, 1260, 1178, 942, 880, 855, 775, 650.

(4) Synthesis of S-p'-octyloxyphenyl p-(2-fluorodecyloxy)thiobenzoate 430 mg of p-(2-fluorodecyloxy)benzoic acid was charged in 20 ml of round-bottomed flask, 1 ml of thionyl chloride was added thereto, and the system was subjected to heat-refluxing for 2 hours. The excessive thionyl chloride was removed by distilling, and 2 ml of toluene was added thereto. On the other hand, 350 mg of p-octyloxybenzenethiol, 1 ml of pyridine and 1 ml of toluene were charged into a 20 ml-round-bottomed flask and ice-cooled, and the above-prepared solution of p-(2-fluorodecyloxy)-benzoate in toluene was added thereto dropwise. The mixture was reacted for 4 hours at room temperature, acidified with 1N-hydrochloric acid aqueous solution and the organic layer was extracted with isotropic ether. The resultant isopropyl ether solution was washed with water until neutralily and dried on sodium sulfate, followed by removal of the solvent by distillation. The residue was further purified by silica gel column chromatography with benzene as an eluent, followed by recrystallization from a mixture solvent of ethyl acetate and ethanol to obtain 350 mg of S-p-octyloxyphenyl p-(2-fluorodecyloxy) thiobenzoate.

Phase transition temperature:

$$\text{Cryst.} \underset{77}{\overset{89}{\rightleftarrows}} \text{SmC*} \underset{98}{\overset{98}{\rightleftarrows}} \text{Ch.} \underset{99}{\overset{100}{\rightleftarrows}} \text{Iso.}$$

EXAMPLES 18–22

Mesomorphic compounds shown in the following Table 5 were prepared according to a process similar to one in Example 16 or 17. The phase transition temperatures of the mesomorphic compounds obtained are also shown in the following Table 5.

TABLE 5

| Example | R$_{10}$ | | Phase transition temperature (°C.) |
|---|---|---|---|
| 16 | n-C$_6$H$_{13}$ | 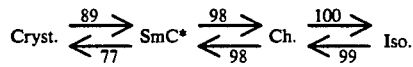 | Cryst. $\overset{85}{\rightarrow}$ SmA $\underset{95}{\overset{96}{\rightleftarrows}}$ Iso. , 73 SmC* 82 |

TABLE 5-continued $$R_{10}-\underset{*}{C}HCH_2-O{-}\!\!\left(\!\!\bigcirc\!\!\right)\!\!_{\overline{n2}}\!\!-\!\!\underset{\underset{O}{\|}}{C}-Z{-}(A_{10})_{\overline{m2}}{-}(A_{11})_{\overline{n2}}{-}X_{10}-R_{11}$$

$$-\!\!\left(\!\!\bigcirc\!\!\right)\!\!_{\overline{n2}}\!\!-\!\!\underset{\underset{O}{\|}}{CA}(A_{10})_{\overline{m2}}{-}(A_{11})_{\overline{n2}}{-}X_{10}-R_{11}$$

| Example | $R_{10}$ |  | Phase transition temperature (°C.) |
|---|---|---|---|
| 17 | n-$C_8H_{17}$ | 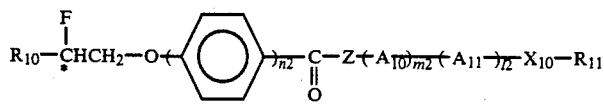 | Cryst. $\underset{77}{\overset{89}{\rightleftarrows}}$ SmC* $\underset{98}{\overset{98}{\rightleftarrows}}$ Ch. $\underset{99}{\overset{100}{\rightleftarrows}}$ Iso. |
| 18 | n-$C_6H_{13}$ | 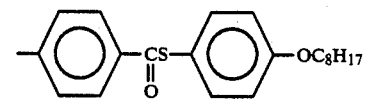 | Cryst. $\underset{67}{\overset{79}{\rightleftarrows}}$ SmC* $\underset{88}{\overset{89}{\rightleftarrows}}$ Ch. $\underset{99}{\overset{100}{\rightleftarrows}}$ Iso. |
| 19 | n-$C_6H_{13}$ | 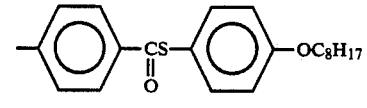 | Cryst. $\underset{65}{\overset{73}{\rightleftarrows}}$ SmA $\underset{81}{\overset{82}{\rightleftarrows}}$ Iso. |
| 20 | n-$C_6H_{13}$ | 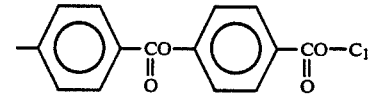 | Cryst. $\overset{97}{\longrightarrow}$ SmC* $\underset{132}{\overset{133}{\rightleftarrows}}$ SmA $\underset{182}{\overset{183}{\rightleftarrows}}$ Iso.<br>66 ↖ ↙ 88<br>$S_{13}$ |
| 21 | n-$C_6H_{13}$ | 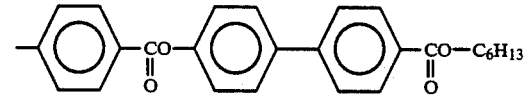 | Cryst. $\underset{97}{\overset{106}{\rightleftarrows}}$ SmC* $\underset{126}{\overset{126}{\rightleftarrows}}$ SmA $\underset{174}{\overset{175}{\rightleftarrows}}$ Iso. |
| 22 | n-$C_8H_{17}$ | 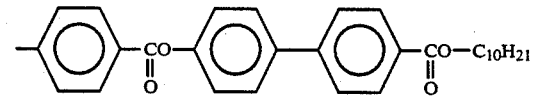 | Cryst. $\overset{92}{\longrightarrow}$ Iso.<br>70 ↖ ↙ 87<br>SmC* $\underset{81}{\longleftarrow}$ SmA |

EXAMPLE 23

The following liquid crystal composition containing the fluoroalkane derivative produced in Example 16 was prepared.

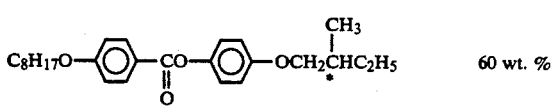 60 wt. %

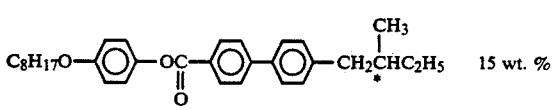 15 wt. %

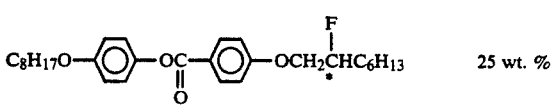 25 wt. %

The above liquid crystal composition was disposed in a 2 μm-thick layer between a pair of electrode plates each provided with a rubbed polyimide film coating electrodes to produce a liquid crystal cell. The cell was driven at 45° C. by application of driving voltages of ±15 volts and a pulse duration of 500 μsec, whereby a good switching state was obtained at a contrast 20.

EXAMPLES 24-29

Liquid crystal cells were prepared similarly as in Example 23 except that the fluoroalkane derivatives prepared in Examples 17-22, respectively, were used instead of the mesomorphic compound of Example 16 represented by the formula:

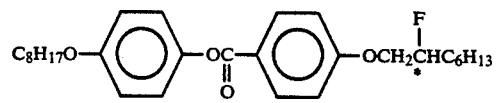

The thus prepared six liquid crystal cells were under the same conditions as in Example 23 to provide switching states respectively at good contrasts.

EXAMPLE 30

A liquid crystal composition was prepared by adding 5 wt. parts of the fluoroalkane derivative according to Example 16 to 95 wt. parts of p,p'-pentylazoxybenzene. A TN (twisted nematic) cell obtained by using the liquid crystal composition was observed to have remarkably reduced reverse domain compared with a TN cell prepared by not using the fluoroalkane derivative.

As explained above, according to the present invention, there are obtained a liquid crystal composition having an enlarged temperature region of chiral smectic phase, and also a liquid crystal device which has an excellent responsive characteristic at a low temperature region, is free of remarkable change in response speed due to temperature change and is thus excellent in display characteristics. According to the present invention, there is provided a ferro-electric liquid crystal device comprising a liquid crystal composition containing at least one chiral smectic mesomorphic compound having a $P_S$ (at $T-T_C=15°$ C.) of 8 nC/cm$^2$ or above, preferably 10 nC/cm$^2$ or above, more preferably 20 nC/cm$^2$ or above, and at least one chiral smectic mesomorphic compound having a $P_S$ (at $T-T_C=15°$ C.) of $-8$ nC/cm$^2$ or below, preferably $-10$ nC/cm$^2$ or below, more preferably $-20$ nC/cm$^2$ or above. By using the ferroelectric liquid crystal device, there is provided a display device or shutter device which has an enlarged tilt angle, excellent transmittance and contrast, high-speed responsive characteristic, a large pixel density and a large area.

According to the present invention, there is further provided a class of optically active substances represented by the formula (I), inclusive of some represented by the above formulas (3) and (4), having a fluorine atom having a large dipole moment directly connected to the asymmetric carbon atom. It is also possible to prevent occurrence of reverse domain in a TN-type liquid crystal composition or improve characteristics such as a responsiveness to an electric field of a chiral nematic liquid crystal or chiral smectic liquid crystal and control the liquid crystal state, by adding at least one species of the optically active substance.

What is claimed is:

1. A fluoroalkane derivative represented by the formula (I):

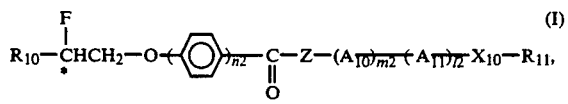

wherein $R_{10}$ denotes an alkyl group having 1–16 carbon atoms; C* denotes an optically active asymmetric carbon atom; $R_{11}$ denotes an alkyl group having 1–16 carbon atoms; Z denotes —O— or —S—; $X_{10}$ denotes a single bond, —O—, or

$A_{10}$ and $A_{11}$ denote a phenylene group

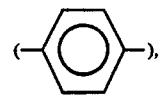

a cyclohexylene group

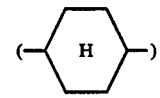

or a pyrimidinylene group

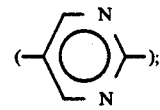

n2 is 1 or 2; l2 and m2 are 0 or a positive integer satisfying the relation l2+m2=1 or 2.

2. A fluoroalkane derivative according to claim 1, which is p'-n-heptyloxyphenyl p-2-fluorohexyloxybenzoate.

3. A fluoroalkane derivative according to claim 1, which is p'-n-dodecyloxyphenyl p-2-fluoroheptyloxybenzoate.

4. A fluoroalkane derivative according to claim 1, which is p'-n-octyloxyphenyl p-2-fluorooctyloxybenzoate.

5. A fluoroalkane derivative according to claim 1, which is p-40 -n-decyloxyphenyl p-2-fluorononyloxybenzoate.

6. A fluoroalkane derivative according to claim 1, which is p'-n-octyloxyphenyl p-2-fluorodecyloxybenzoate.

7. A fluoroalkane derivative according to claim 1, which is p-40 -n-tetradecyloxyphenyl p-2-fluorododecyloxybenzoate.

8. A fluoroalkane derivative according to claim 1, which is p-n-nonyloxyphenyl p-2-fluorododecyloxybenzoate.

9. A fluoroalkane derivative according to claim 1, which is p'-n-hexyloxyphenyl p-2-fluorohexadecyloxybenzoate.

* * * * *

UNITED STATES PATENT AND TRADEMARK OFFICE
CERTIFICATE OF CORRECTION

PATENT NO. : 5,328,639
DATED : July 12, 1994
INVENTOR(S) : HIROYUKI NOHIRA, ET AL.

It is certified that error appears in the above-identified patent and that said Letters Patent is hereby corrected as shown below:

ON TITLE PAGE

In [56] References Cited, under FOREIGN PATENT DOCUMENTS:
"240385  10/1986  Fed. Rep. of Germany" should read
--240385  10/1986  Dem. Rep. of Germany--.

IN THE DRAWINGS

Sheet 3 of 4, FIG. 6: "RESPONS" should read --RESPONSE--.

COLUMN 1

Line 45, "ferro-electric" should read --ferroelectric--.

COLUMN 2

Line 20, "seldome" should read --seldom--.
Line 40, "ferro-electric" should read --ferroelectric--.

COLUMN 3

Line 11, "light," should read --light;--.
Line 29, "an" should read --a--.

COLUMN 5

Line 47, "lienar" should read --linear--.

COLUMN 6

Line 18, "may be" should read --may for--.

UNITED STATES PATENT AND TRADEMARK OFFICE
CERTIFICATE OF CORRECTION

PATENT NO. : 5,328,639
DATED : July 12, 1994
INVENTOR(S) : HIROYUKI NOHIRA, ET AL.

It is certified that error appears in the above-identified patent and that said Letters Patent is hereby corrected as shown below:

COLUMN 34

Line 34, "for ," should read --for--.

COLUMN 36

Line 52, "he" should read --be--.

COLUMN 37

Formula I, " $-\overset{}{\underset{\|}{C}}-$ " should read -- $-\overset{}{\underset{\overset{\|}{O}}{C}}-$ --.

COLUMN 40

Line 30, "represent" should read --represented--.

COLUMN 41

Formula <7>, " $\underset{C_2H_5CHCH_2OCOC}{\overset{CH_3}{|}}$ " should read -- $\underset{C_2H_5CHCH_2OCO}{\overset{CH_3}{|}}$ -- and " <6>
<8> " should read -- <6>
<7>
<8> --.

COLUMN 43

Formula <11>, "4-carboxylate" should read --4'-carboxylate--.
Formula <12>, "4-hyexylophenyl4-4-" should read --4-hexyloxyphenyl-4- --.

UNITED STATES PATENT AND TRADEMARK OFFICE
CERTIFICATE OF CORRECTION

PATENT NO. : 5,328,639
DATED : July 12, 1994
INVENTOR(S) : HIROYUKI NOHIRA, ET AL.

It is certified that error appears in the above-identified patent and that said Letters Patent is hereby corrected as shown below:

COLUMN 45

Formula <15>, "4,4'-decyloxyzaoxybenzene" should read --4,4'-decyloxyazoxybenzene--.
Line 55, "tot he" should read --to the--.

COLUMN 46

Line 61, "regin." should read --resin.--.

COLUMN 47

Line 13, "specers" should read --spacers--.
Line 42, "tile" should read --tilt--.

COLUMN 51

Line 6, "15% 5% 10% 15%" should read --15%, 5%, 10%, 15%,--.
Line 39, "15 second" should read --15 seconds--.

COLUMN 52

Line 15, "a" should read --an--.

COLUMN 55

Line 13, "when" should be deleted.
Line 22, "arised" should read --arose--.

COLUMN 57

Line 50, "subjected" should read --subjected to--.

UNITED STATES PATENT AND TRADEMARK OFFICE
CERTIFICATE OF CORRECTION

PATENT NO. : 5,328,639
DATED : July 12, 1994
INVENTOR(S) : HIROYUKI NOHIRA, ET AL.

It is certified that error appears in the above-identified patent and that said Letters Patent is hereby corrected as shown below:

COLUMN 59

Line 19, "$OCH_2\overset{F}{\underset{*}{C}}HOC_8H_{17}$" should read --$OCH_2\overset{F}{\underset{*}{C}}HC_8H_{17}$--.

Line 25, "$OCH_2\overset{F}{\underset{*}{C}}HOC_6H_{13}$" should read --$OCH_2\overset{F}{\underset{*}{C}}HC_6H_{13}$--.

COLUMN 61

Line 46, "(17.4 raM)" should read --(17.4 mM)--.

COLUMN 62

Line 47, "Nail" should read --NaH--.

COLUMN 63

Line 33, "iropropyl" should read --isopropyl--.

COLUMN 64

Line 28, "isotropic" should read --isopropyl--.
Line 29, "neutralily" should read --neutral--.

COLUMN 65

Line 67, "electrodes" should read --electrode--.

UNITED STATES PATENT AND TRADEMARK OFFICE
CERTIFICATE OF CORRECTION

PATENT NO. : 5,328,639
DATED : July 12, 1994
INVENTOR(S) : HIROYUKI NOHIRA, ET AL.

It is certified that error appears in the above-identified patent and that said Letters Patent is hereby corrected as shown below:

<u>COLUMN 68</u>

Line 20, "pyrimidinyulene" should read --pyrimidinylene--.
Line 40, "p-40 -n-decyloxyphenyl" should read --p'-n-decyloxyphenyl--.
Line 46, "p-40 -n-tetradecyloxyphenyl" should read --p'-n-tetradecyloxyphenyl--.
Line 49, "p-n-nonyloxyphenyl" should read --p'-n-nonyloxyphenyl--.

Signed and Sealed this

Thirty-first Day of January, 1995

Attest:

BRUCE LEHMAN

*Attesting Officer*    Commissioner of Patents and Trademarks